US010251780B2

(12) United States Patent
Tai et al.

(10) Patent No.: US 10,251,780 B2
(45) Date of Patent: Apr. 9, 2019

(54) 3-COIL WIRELESS POWER TRANSFER SYSTEM FOR EYE IMPLANTS

(71) Applicants: California Institute of Technology, Pasadena, CA (US); University of Southern California, Los Angeles, CA (US)

(72) Inventors: Yu-Chong Tai, Pasadena, CA (US); Yu Zhao, Pasadena, CA (US); Mark S. Humayun, Glendale, CA (US); James D. Weiland, Valencia, CA (US)

(73) Assignees: California Institute of Technology, Pasadena, CA (US); University of Southern California, Los Angeles, CA (US)

(*) Notice: Subject to any disclaimer, the term of this patent is extended or adjusted under 35 U.S.C. 154(b) by 48 days.

(21) Appl. No.: 14/749,487

(22) Filed: Jun. 24, 2015

(65) Prior Publication Data

US 2015/0290466 A1 Oct. 15, 2015

Related U.S. Application Data

(62) Division of application No. 13/973,847, filed on Aug. 22, 2013, now Pat. No. 9,078,743.

(30) Foreign Application Priority Data

Aug. 22, 2013 (WO) .................. PCT/US2013/05623

(51) Int. Cl.
*A61N 1/378* (2006.01)
*C23F 1/00* (2006.01)
(Continued)

(52) U.S. Cl.
CPC ............ *A61F 9/007* (2013.01); *A61N 1/0543* (2013.01); *A61N 1/36046* (2013.01);
(Continued)

(58) Field of Classification Search
CPC ......... A61F 9/007; A61B 5/05; A61N 1/0543; A61N 1/36046; A61N 1/3787;
(Continued)

(56) References Cited

U.S. PATENT DOCUMENTS 1,547,507 A * 7/1925 Leib ....................... H01F 17/04
336/134
4,126,844 A * 11/1978 Hollister .................. H01F 5/02
29/605
(Continued)

FOREIGN PATENT DOCUMENTS

| WO | 2006116625 | 11/2006 |
| WO | 2011120540 | 10/2011 |
| WO | 2014031878 | 2/2014 |

OTHER PUBLICATIONS

U.S. Appl. No. 13/973,847, "Advisory Action", dated Jan. 23, 2015, 3 pages.
(Continued)

*Primary Examiner* — Richard Isla
*Assistant Examiner* — Dung V Bui
(74) *Attorney, Agent, or Firm* — Kilpatrick Townsend & Stockton LLP

(57) ABSTRACT

A three-coil electromagnetic induction power transfer system is disclosed for epiretinal prostheses and other implants. A third, buffer coil is disposed between an external transmitting coil and a receiver coil buried within the body to improve efficiency and robustness to misalignments. One or more of the coils can be manufactured using micromechanical machining techniques to lay out conductors in a ribbon
(Continued)

of biocompatible insulator, folding lengths of the insulated conductor traces longitudinally over one another, and then spiraling them into a ring. The traces change axial position in the ring by shifting across fold lines. One or more U-shaped sections on the traces can be folded so that adjacent traces can project opposite one another, lengthening the resulting ribbon that can be wound into a coil.

20 Claims, 19 Drawing Sheets

Related U.S. Application Data

(60) Provisional application No. 61/692,138, filed on Aug. 22, 2012.

(51) Int. Cl.
| | |
|---|---|
| H01F 27/28 | (2006.01) |
| A61N 1/36 | (2006.01) |
| A61F 9/007 | (2006.01) |
| A61N 1/05 | (2006.01) |

(52) U.S. Cl.
CPC .............. *A61N 1/3787* (2013.01); *C23F 1/00* (2013.01); *H01F 27/2804* (2013.01); *A61N 1/0529* (2013.01); *A61N 1/0551* (2013.01); *A61N 1/3605* (2013.01); *H01F 2027/2809* (2013.01)

(58) Field of Classification Search
CPC .. A61N 1/0529; A61N 1/0551; A61N 1/3605; C23F 1/00; C23F 1/02; H01F 27/2804; H01F 27/28; H01F 2027/2809
USPC ............................................... 320/108; 428/8
See application file for complete search history.

(56) References Cited

U.S. PATENT DOCUMENTS

| | | | | | |
|---|---|---|---|---|---|
| 4,792,790 | A | * | 12/1988 | Reeb | G06K 19/0672 257/E27.114 |
| 4,935,093 | A | * | 6/1990 | Reeb | G06K 19/0672 216/20 |
| 5,554,096 | A | * | 9/1996 | Ball | H04R 11/02 381/322 |
| 5,935,155 | A | * | 8/1999 | Humayun | A61M 5/3213 607/54 |
| 6,025,725 | A | * | 2/2000 | Gershenfeld | H01F 17/0006 324/652 |
| 6,324,429 | B1 | * | 11/2001 | Shire | A61N 1/0543 607/54 |
| 6,458,157 | B1 | * | 10/2002 | Suaning | A61F 2/14 623/6.63 |
| 6,976,998 | B2 | | 12/2005 | Rizzo et al. | |
| 7,311,723 | B2 | * | 12/2007 | Seibel | A61F 9/08 128/898 |
| 7,447,548 | B2 | | 11/2008 | Eckmiller | |
| 7,774,931 | B2 | | 8/2010 | Tai et al. | |
| 7,976,862 | B2 | * | 7/2011 | Anderson | A61K 31/58 424/422 |
| 8,131,378 | B2 | | 3/2012 | Greenberg et al. | |
| 8,447,410 | B2 | | 5/2013 | Greenberg et al. | |
| 8,706,243 | B2 | * | 4/2014 | Gefen | A61F 2/14 607/53 |
| 9,078,743 | B2 | | 7/2015 | Tai et al. | |
| 2002/0091421 | A1 | | 7/2002 | Greenberg et al. | |
| 2002/0198573 | A1 | * | 12/2002 | Nisch | A61F 2/14 607/54 |
| 2003/0093132 | A1 | * | 5/2003 | Eckmiller | A61N 1/36046 607/54 |
| 2003/0109926 | A1 | * | 6/2003 | Portney | A61F 2/1602 623/6.37 |
| 2003/0158588 | A1 | * | 8/2003 | Rizzo | A61F 2/14 607/54 |
| 2003/0233134 | A1 | | 12/2003 | Greenberg et al. | |
| 2004/0102843 | A1 | * | 5/2004 | Yagi | A61F 2/14 623/4.1 |
| 2004/0224002 | A1 | | 11/2004 | Fishman et al. | |
| 2004/0260372 | A1 | | 12/2004 | Canfield et al. | |
| 2005/0222624 | A1 | * | 10/2005 | Greenberg | A61N 1/0543 607/2 |
| 2006/0121639 | A1 | | 6/2006 | Tai et al. | |
| 2006/0155372 | A1 | * | 7/2006 | Coroneo | A61F 2/1635 623/4.1 |
| 2006/0161225 | A1 | * | 7/2006 | Sormann | A61B 5/0031 607/61 |
| 2006/0200218 | A1 | | 9/2006 | Wahlstrand | |
| 2008/0021525 | A1 | * | 1/2008 | Solzbacher | A61N 2/02 607/61 |
| 2008/0071313 | A1 | * | 3/2008 | Stevenson | A61N 1/056 607/2 |
| 2008/0086183 | A1 | | 4/2008 | Greenberg et al. | |
| 2008/0262611 | A1 | | 10/2008 | Li et al. | |
| 2010/0259352 | A1 | * | 10/2010 | Yan | H01F 5/003 336/200 |
| 2010/0265680 | A1 | * | 10/2010 | Tai | A61B 5/0031 361/760 |
| 2012/0116507 | A1 | * | 5/2012 | Ng | A61N 1/0543 623/6.63 |
| 2014/0058506 | A1 | | 2/2014 | Tai et al. | |

OTHER PUBLICATIONS

U.S. Appl. No. 13/973,847, "Final Office Action", dated Nov. 10, 2014, 12 pages.
U.S. Appl. No. 13/973,847, "Non-Final Office Action", dated Jul. 29, 2014, 10 pages.
U.S. Appl. No. 13/973,847, "Notice of Allowance", dated Mar. 5, 2015, 7 pages.
CN201380042808.X, "Office Action", dated Sep. 23, 2016, 3 pages.
EP13830601.4, "Extended European Search Report", dated May 11, 2016, 5 pages.
Humayun et al., Artificial Sight: Basic Research, Biomedical Engineering and Clinical Advances, Jun. 2007 edition, Springer.
Kendir et al., "An Optimal Design Methodology for Inductive Power Link with Class-E Amplifier," IEEE Transaction on Circuits and Systems-I: Regular Papers, May 2005, vol. 52(5), pp. 857-866.
Kelly et al., "The Boston Retinal Prosthesis, A 15-Channel Hermetic Wireless Neural Stimulator," Applied Sciences in Biomedical Communication Technologies, Nov. 24-27, 2009 Conference, $2^{nd}$ International Symposium, pp. 1-6.
Kelly et al., "Optimal primary coil size for wireless power telemetry to medical implants," Applied Sciences in Biomedical and Communication Technologies, Nov. 7-10, 2010 Conference, $3^{rd}$ International Symposium.
Kiani et al., "Design and Optimization of a 3-Coil Inductive Link for Efficient Wireless Power Transmission," Biomedical Circuits and Systems, IEEE Transactions, Dec. 2011, vol. 5(6), pp. 579-591.
Koch et al., "First Results of a Study on a Completely Implanted Retinal Prosthesis in Blind Humans," IEEE Sensors, Oct. 26-29, 2008 Conference, pp. 1237-1240.
Li et al., "Integrated Flexible Ocular Coil for Power and Data Transfer in Retinal Prostheses," Proceedings of the 2005 IEEE Engineering in Medicine and Biology $27^{th}$ Annual Conference, Sep. 1-4, 2006, Shanghai, China, pp. 1028-1031.
Lin, Thesis, Feb. 2012, MEMS for Glaucoma.
Lotfi, Chapter 1—"Building the bionic eye: an emerging reality and opportunity," Progress in Brain Research, Sep. 2011, C.E.C.J.F.K. Andrea Green and L. Franco, Elsevier, vol. 192, pp. 3-15.
Mokwa, "Retinal implants to restore vision in blind people," Solid-State Sensors, Actuators and Microsystems Conference, (Transducers) Jun. 2011, $16^{th}$ International, pp. 2825-2830.

(56) References Cited

OTHER PUBLICATIONS

Ng et al., "Wireless power delivery for retinal prostheses," Engineering in Medicine and Biology Society, EMBC 2011, Annual International Conference of the IEEE EMBS Boston Massachusetts, Aug. 30-Sep. 3, 2011, pp. 8356-8360.
RamRakhyani et al., "Design and Optimization of Resonance-Based Efficient Wireless Power Delivery Systems for Biomedical Implants," Biomedical Circuits and Systems, IEEE Transactions, Feb. 2011, vol. 5(1), pp. 48-63.
Second Sight, Argus II Retinal Prostheses, http://2-sight.eu/, retrieved on or about Nov. 8, 2011.
Weiland et al., "Retinal Prosthesis," Annual Review of Biomedical Engineering, Mar. 2005, vol. 7(1), pp. 361-401.
Zhao et al., "A MEMS intraocular origami coil," Solid-State Sensors, Actuators and Microsystems Conference (Transducers) Jun. 2011, 16$^{th}$ International, pp. 2172-2175.
PCT application No. PCT/US2013/056236, International Search Report and Written Opinion, dated Jan. 28, 2014, 16 pages.

\* cited by examiner

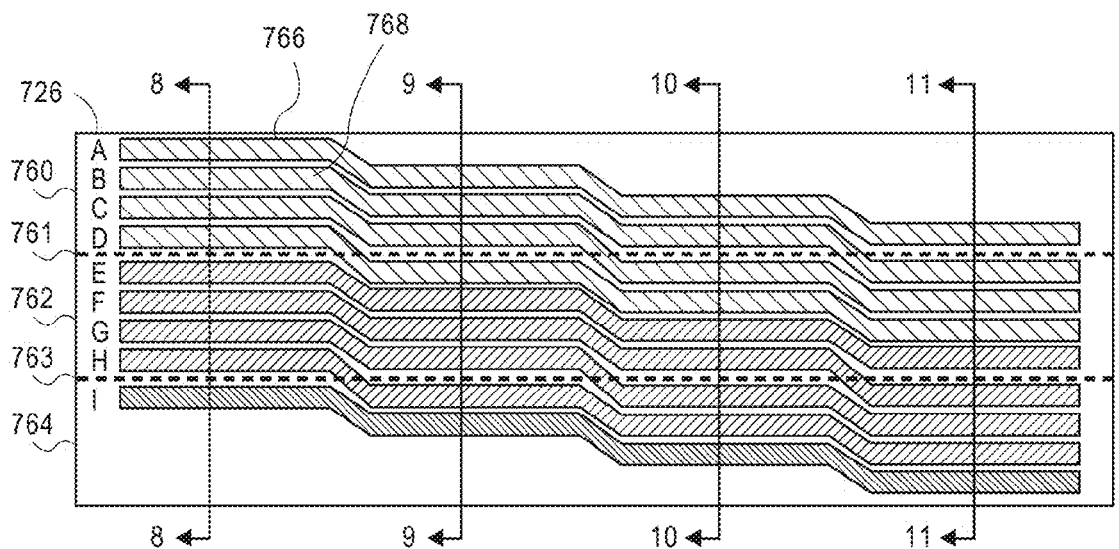
FIG. 7
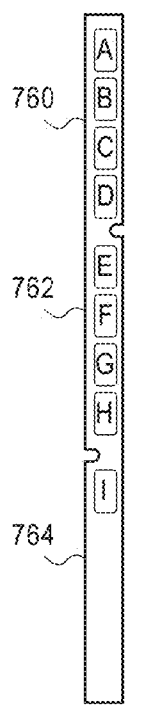 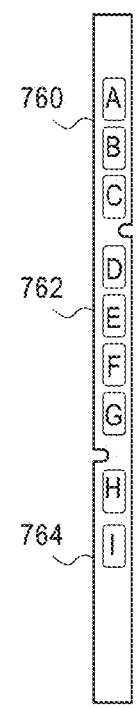 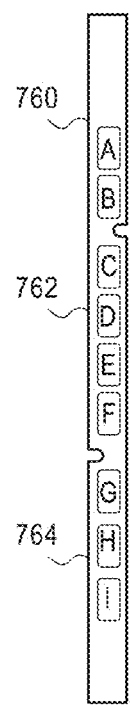 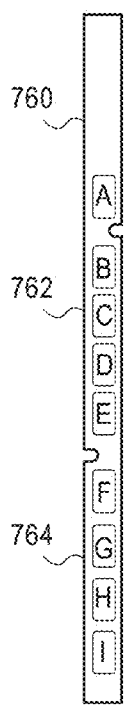
FIG. 8  FIG. 9  FIG. 10  FIG. 11

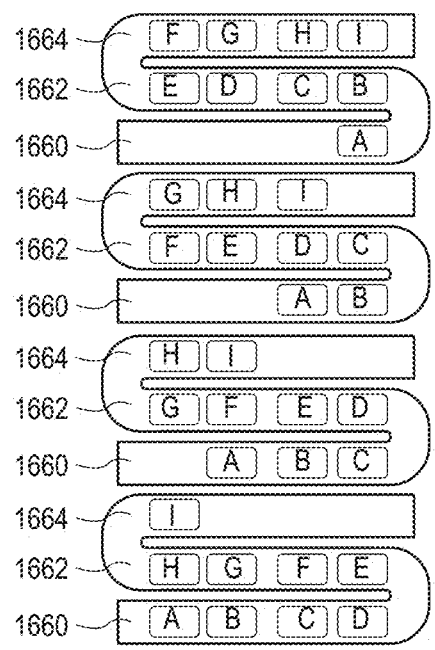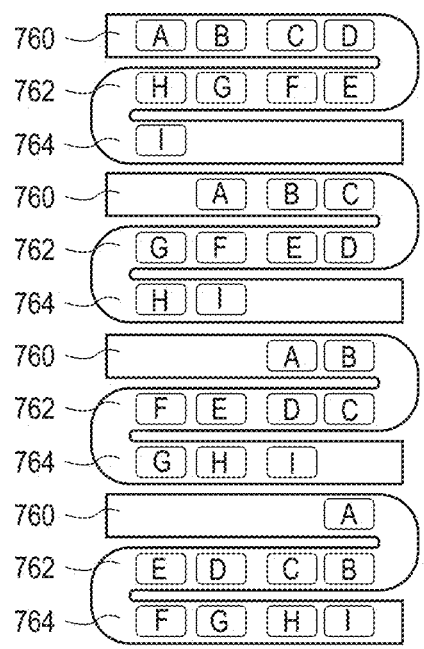
FIG. 16

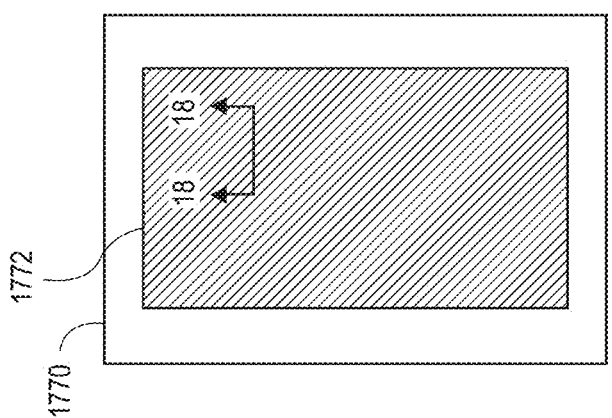
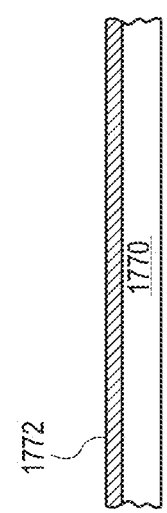
FIG. 17     FIG. 18
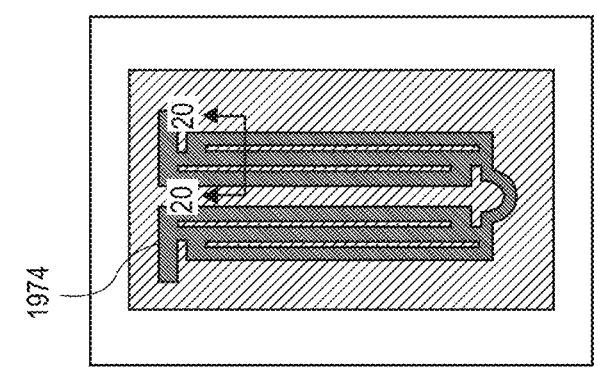
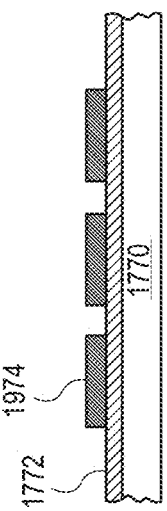
FIG. 19     FIG. 20
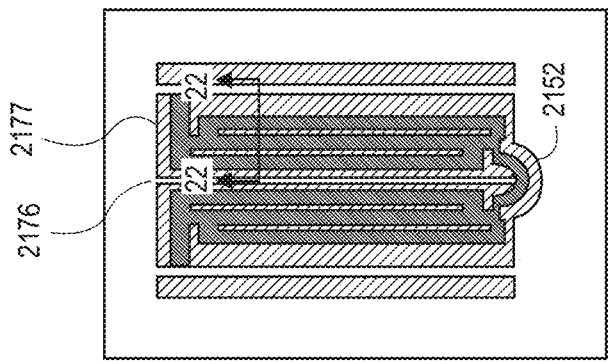
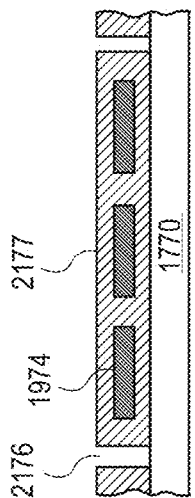
FIG. 21     FIG. 22

3-COIL WIRELESS POWER TRANSFER SYSTEM FOR EYE IMPLANTS

CROSS-REFERENCES TO RELATED APPLICATIONS

This application is a divisional application of U.S. application Ser. No. 13/973,847, filed Aug. 22, 2013, which claims the benefit of U.S. Provisional Application No. 61/692,138, filed Aug. 22, 2012, which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under EEC0310723 awarded by the National Science Foundation. The government has certain rights in the invention.

BACKGROUND

1. Field of the Art

Embodiments of the present invention generally relate to wireless power transfer to surgically implanted prostheses, in particular, to a three-coil power transfer system with one of the coils being a fully intraocular coil.

2. Description of the Related Art

Age-related macular degeneration (AMD) and retinitis pigmentosa (RP) are two most common outer-retina degenerative diseases of the human eye. There is promise in the use of retinal prostheses in order to allow people afflicted with the diseases to see. Retinal prostheses, which bypass the defective outer-retina photoreceptors and electrically stimulate the inner-retina neurons directly, have allowed some blind people with AMD and RP to perceive light.

It is recognized that these early prostheses only involve a very small number of stimulating electrodes on the neurons. To realize facial recognition or large-sized letter reading, next-generation retinal prosthetic devices may use 1024 or more stimulating electrodes.

Unfortunately, the high-resolution sensors and processors have relatively high power consumption, for example, greater than 100 milliwatts (mW). Current battery technology limits their usefulness for such implants, so power is preferably drawn from outside the body. Cables tend to be unwieldy for connecting a patient's eye to an external power source, so wireless power transfer is preferred.

Electromagnetic inductive coupling between two coils has been widely studied and optimized for wirelessly powering retinal prosthetic devices. However, because of the extremely demanding physical constraints in and around the eye, the physical placement of the implanted receiver coil remains a matter of ongoing debate. There are tradeoffs between the power-transfer capability, surgical risk and long-term implantation. While there are fewer constraints on a transmitting coil, which is outside the body, it cannot be too powerful lest it heat the receiver coil too much or subject the patient to unacceptable levels of electromagnetic fields.

Generally, the inductive link efficiency between two coils is proportional to the square of the coupling coefficient (k) and the respective quality factors (Qs) of coupled coils. Wireless power transfer naturally involves no magnetic transformer core around which a primary winding and a secondary winding are wound as in a conventional electrical transformer. Instead, wireless inductively-linked coils are coupled through the air (or other intervening media).

In the prior art, to compensate for the low-efficiency of this air-cored coupling and satisfy safety limitations, such as heat dissipation, electromagnetic field exposure, etc., the receiver coils are placed extraocular and connected to the electrodes sitting intraocular through a cable that penetrates the eyeball. To penetrate the eyeball into the inside, one typically penetrates the eye's sclera and choroid. This trans-sclera, trans-choroid cable potentially causes infection and hypotony in the long-term implantation.

Fully-intraocular retinal implants have been attempted that place the receiver coil inside the lens capsule after removing the natural lens. However, with a 25 millimeter (mm) (1-inch) separation between the transmitter and receiver coils, this 2-coil configuration suffers low efficiency (e.g., 7%) from the limited Q of the receiver coil and the small coupling coefficient k between the coupled coils.

There exists a need in the art for more efficient wireless electrical power transfer methods for retinal implants.

BRIEF SUMMARY

Generally, a third coil, called a "buffer coil," is introduced between the transmitter coil and receiver coil to increase power transfer efficiency between the transmitter coil and receiver coil. In particular with the physical constraints of the human eye, an intervening buffer coil fits into the available spaces well. In some instances, it may not need to be surgically implanted at all, but instead worn by a patient as a sclera lens.

The buffer coil and/or receiver coil can be geometrically oblong, such as an oval, in order to account for greater movement of the eye in the horizontal direction as opposed to the vertical direction.

A high-Q receiver coil of the size that can fit in tight places within the human body can be manufactured using both micromachining—and origami—techniques. Thin, conductive traces are laid out on a flat substrate within a flexible insulator and then peeled from the substrate. Swaths of traces in the flexible insulator are then folded over one another. The resulting folded traces are coiled into a ring. The ring, or coil, can be pinched radially so that it can be inserted through small incisions, and once released will snap back to its ring shape.

Electrical resistance caused by the skin effect can be minimized by sizing the electrical traces appropriately for the electromagnetic induction frequency. Further, the traces can be laid out so when they are wound into the coil, the traces shift their axial positions so as to share the (axial) outside positions, thus minimizing resistance caused by the proximity effect. The traces can shift axial positions by having an outermost trace pass over a fold line (i.e., a crease) while an inner trace takes its place at the outermost position.

Because silicon wafer substrates can be small, a U-shaped section of traces can effectively double the length of the traces to be coiled into a coil. Multiple U-shaped sections can triple, quadruple, etc. the length of the traces. Folding the U-shaped region up and then folding the two sides of the U together results in the traces that were once adjacent on the substrate being disposed in opposite directions from one another.

The receiver coil can be fitted with an air-filled chamber, acting as a floatation device, and therefore meet effective mass constraints within they eye. The chamber can be filled with gas by a surgeon and or opportunistically capture air bubbles.

Although many of the embodiments discussed refer to the human eye, devices and methods for implanting into other portions of the body and other animal species are envisioned. Anywhere that wireless electrical power transfer must be efficient may find use from aspects taught herein.

Some embodiments of the present invention relate to an inductively-powered eye implant apparatus. The apparatus includes a buffer coil adapted to be affixed external to a sclera of an eye, the buffer coil having a conductor covered by a biocompatible layer, a receiver coil adapted for implantation within the eye, the receiver coil having a conductor covered by a biocompatible layer, the receiver coil adapted for receiving electrical power by electromagnetic induction through the buffer coil from a transmitter coil, the buffer coil and receiving coil adapted to be electromagnetically coupled when affixed external to and implanted within the eye, respectively, and a processing circuit connected with the conductor of the receiver coil and configured to receive electrical power from the receiver coil.

The apparatus can include an array of stimulating electrodes adapted to be connected with inner retina neurons in the eye and connected with the processing circuit, and an electrical cable coupling the receiver coil with the array. The buffer coil can be suitable for mounting around the cornea and under the conjunctiva of the eye, or there can be a sclera lens encasing the buffer coil, the sclera lens adapted to be worn on the sclera to thereby affix the buffer coil external to the sclera of the eye.

In some embodiments, the buffer coil is adapted to be affixed to a side of the eye external to the sclera, and the receiver coil is adapted for mounting within a vitreous body of the eye inside the sclera to an internal side of the eye.

The apparatus can have a buffer coil that is circular and have an outer diameter equal to or between about 19 millimeters and 20 millimeters. Or the buffer coil can be oval and have an outer minor axis of about 19 millimeters and an outer major axis of about 24 millimeters, the buffer coil adapted to be affixed external to the sclera such that the outer major axis is substantially horizontal. The apparatus can have a buffer coil or receiver coil that is in a polygon shape as viewed from an axial direction.

Optionally, the receiver coil of the apparatus is produced by etching conductor traces on an electrically insulative sheet, depositing electrical insulator over the etched conductor traces sufficient to embed the etched conductor traces in a biocompatible layer, folding the sheet over onto itself, stacking the embedded conductor traces, and then winding the folded sheet in a spiral to form a closed shape. Further, the conductor traces on the electrically insulative sheet can include a U-shaped region connecting two lengths of conductor traces that project in a same direction from the U-shaped region. The production of the receiver coil can further be produced by folding the sheet, before the winding, such that the U-shaped region is perpendicular to the sheet, and then folding the U-shaped region such that the lengths of conductor traces project in opposite directions from the U-shaped region.

Some embodiments relate to a method of efficiently receiving power inside an eye for an intraocular electronic device without an sclera-piercing cable. The method includes receiving, into a buffer coil affixed external to a sclera of an eye, a varying magnetic field by way of a first electromagnetic induction, the varying magnetic field causing current in the buffer coil, inducing current, within a receiver coil within the eye, by way of a second electromagnetic induction from the current in the buffer coil to the receiver coil, and powering an intraocular electronic device using the induced current from the receiver coil.

The method can further include rectifying the induced current from the receiver coil to generate direct current.

Some embodiments relate to a method of manufacturing a coil suitable for electromagnetic induction. The method can include etching conductor traces on a substrate, the conductor traces underlaid by a sheet of flexible, biocompatible electrical insulator, depositing more electrical insulator over the conductor traces to embed the conductor traces in the electrical insulator, peeling the insulator embedded conductor traces from the substrate to release a flexible ribbon of the embedded conductor traces, folding the ribbon along one or more longitudinal creases to stack the embedded conductor traces, and winding the ribbon in a spiral to form a closed shape, thereby forming a coil of stacked conductor traces.

The method can further include radially pinching the coil, and passing the pinched coil through an incision in an eye. It can also include connecting pads or leads of the conductor traces to a processing circuit, connecting the processing circuit to an array of stimulating electrodes adapted to be connected with inner-retina neurons in an eye, and coupling an electrical cable between the coil and the array.

The method can include sealing air within a chamber, and rigidly attaching the chamber to the coil, thereby adding buoyancy to the coil.

The conductor traces on the sheet can include a U-shaped region, and the method can include connecting two lengths of conductor traces that project in a same direction from the U-shaped region. The method can further include folding the ribbon, before the winding, such that the U-shaped region is perpendicular to the rest of the ribbon, and then folding the U-shaped region such that the lengths of conductor traces project in opposite directions from the U-shaped region.

Some embodiments relate to an inductively-powered implant apparatus. The apparatus includes a buffer coil adapted to be affixed within a portion of a body of a patient, the buffer coil having a conductor covered by a biocompatible layer, a receiver coil adapted for implantation within a deeper portion of the body than the buffer coil, the receiver coil having a conductor covered by a biocompatible layer, the receiver coil adapted for receiving electrical power by electromagnetic induction through the buffer coil from a transmitter coil, the buffer coil and receiving coil adapted to be electromagnetically coupled, and a processing circuit connected with the conductor of the receiver coil and configured to receive electrical power from the receiver coil.

The portion of the body can includes a head and/or skull, and the processing circuit can include a brain pacemaker. The apparatus can include a torso, and the processing circuit can includes a spinal cord stimulator. The apparatus can include a rechargeable battery configured to receive electrical power through and be recharged by the processing circuit.

BRIEF DESCRIPTION OF THE DRAWINGS

FIG. 7 illustrates a ribbon of etched traces on a flat surface in accordance with an embodiment.

FIG. 8 illustrates cross section 8-8 of FIG. 7.

FIG. 9 illustrates cross section 9-9 of FIG. 7.

FIG. 10 illustrates cross section 10-10 of FIG. 7.

FIG. 11 illustrates cross section 11-11 of FIG. 7.

FIG. 16 is a cross section of a wound coil of stacked etched traces, along with additional stacks of traces from a U-turn, in accordance with an embodiment.

FIG. 17 illustrates a flat sheet on a substrate in accordance with an embodiment.

FIG. 18 is cross section 18-18 of FIG. 17.

FIG. 19 illustrates etched conductor traces in accordance with an embodiment.

FIG. 20 is cross section 19-19 of FIG. 19.

FIG. 21 illustrates embedded conductor traces in a biocompatible insulative layer in accordance with an embodiment.

FIG. 22 is cross section 22-22 of FIG. 21.

Figure 1A:
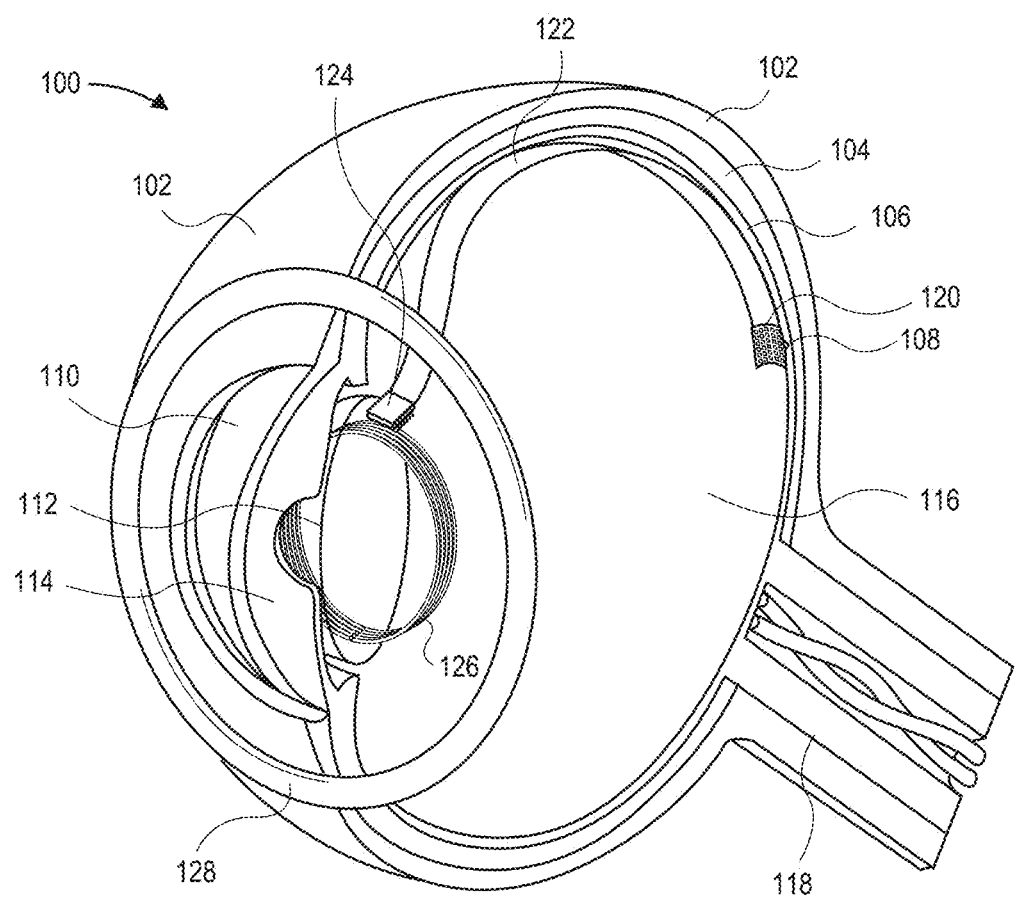
FIG. 1A is a perspective illustration of an eyeball with an inductively-powered eye implant apparatus having a lens-mounted receiver coil in accordance with an embodiment.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

A three-coil power transmission system for implanted devices offers many technical benefits. The third, buffer coil increases efficiency of power transmission between the transmitter coil and receiver coil. It also allows another set of design parameters with which to work so that a receiver coil (or transmitter coil) may be sized for small, constrained spaces. A three-coil structure can tolerate larger misalignments in the X-Y plane between coils than a two-coil structure. This can be important for cases in which the receiver coil is buried in the body and not visible, so an exact determination of its location is unknown. It can also help mitigate voluntary or involuntary movements of a subject, keeping efficiency high. Further, a three-coil structure can tolerate larger angular misalignments between coils than a two-coil structure. The coils do not need to be aligned as much. This may be especially important with blind people who cannot fixate their eyes in a certain position while using retinal implant equipment.

A three-coil system can help in many types of implants, such as intraocular, cortical, and spinal implants. It can be used for imaging, displays, cameras, drug delivery devices, pressure transducers, and other uses that depend on electrical power. Wherever there is a need for efficient wireless power transmission into the body, a third coil may help.

Four, five, six, and greater numbers of coils can be used to further increase efficiency or give more design space so that receiver coils or transmission coils can be redesigned. Multiple coils may be especially useful when the receiver coil is buried deep within the body, far away from the surface.

A coil for electromagnetic induction fabricated using micromachining processes combined with folding offers many technical benefits. Such coils can be manufactured to be extremely small, suitable for high frequencies. Further, resilient coils can be pinched, flexed, and/or folded to fit through snug places and then expand back into shape. Electrical conductor traces can be appropriately sized to have a high surface area-to-volume ratio, minimizing areas of conductor that would not be used because of the skin effect. The skin effect is a description of non-uniform current distribution in a cross section of a conductor at high frequencies. The higher the frequency, the more that the current only flows through the outermost portions (i.e., the skin) of a conductor. Micromachined coils can also be formed to minimize the proximity effect of current at high frequencies. The proximity effect is also a description of non-uniform current distribution in a cross section of nearby conductors at high frequencies. The higher the frequency, the more the current in parallel wires stays away from the opposing wires when the currents travel in the same direction (or stays close to the other wire when the currents travel in opposite directions). A quality factor (Q) for a power coil is defined by $Q = \omega L / R_{ac}$, where $\omega$ is frequency in radians, L is inductance of the coil, and $R_{ac}$ is resistance to alternating current. Therefore, the lower the $R_{ac}$, the higher the Q.

Another benefit is that biocompatible coils can be micromanufactured using readily available biocompatible materials.

A U-shaped section of electrical conductor traces that is later folded to straighten it out offers many technical benefits. A smaller wafer can be used as a substrate for depositing the traces. For example, a 10 centimeter (4 inch) diameter wafer can produce a length of conductors that is 20 centimeters (8 inches) long. For a coil that is 1 centimeter (cm) in diameter, a 20-cm long length allows it to be coiled six times around, as opposed to only three times around for a 10-cm long length.

Other advantages of these and other aspects will be apparent from the specification and drawings. Many of the embodiments are explained with respect to an eye implant; however, other implant uses will be apparent.

It has been found that the lens capsule in an eye is an ideal position to place an intraocular receiver coil. The lens capsule is just large enough for a coil, it is within the sclera, and surgical implantation procedures are well established. After the natural lens is removed, an intraocular coil can be implanted into the lens capsule bag.

Associated with that implant position, two intrinsic challenges for achieving a high-Q coil are the size and equivalent mass. The size of a coil is preferably less than or equal to 10 mm in outer diameter. A diameter of 9 to 10 mm is generally the maximum, with 9.5 mm being the average maximum. The equivalent mass of a coil is preferably equal to or less than 46 milligrams (mg) in saline.

An "equivalent mass" of an item in a liquid is its mass minus the mass of liquid displaced by the volume of item. This accounts for buoyant forces on the item.

A buffer coil can be implanted around the cornea and under the conjunctiva of the eye. A buffer coil with a 20 mm diameter has been found to be large enough to circumscribe a cornea of an adult human eye, and keep away from resting on it. A buffer coil comprising a litz wire having thirty insulated strands of 48 American wire gauge (AWG) wire conductors has been used experimentally to good effect.

The outer diameter of an adult eyeball is generally 23 to 25 mm, with an average of 24 mm. A normal human eye can move horizontally ±30° and vertically ±10°.

A transmitter coil of 42 mm in diameter has been determined to work efficiently with a 10-mm receiver coil in the lens capsule and a 20-mm buffer coil under the conjunctiva. In this configuration, the transmitter coil and receiver coil end up being separated axially by 25 mm, suitable for mounting on a pair of reading glasses.

A 10 megahertz (MHz) carrier frequency has been found to be acceptable due to a tradeoff between the tissue's radio frequency (RF) absorption and the coils Q values. All three coils can be tuned to resonate at the operating frequency with connection to corresponding capacitors in parallel or in series.

FIG. 1A is a perspective, cutaway illustration of an eyeball with an inductively-powered eye implant apparatus having a lens-mounted receiver coil in accordance with an embodiment. Eye 100 includes sclera 102, choroid 104, retina 106, fovea 108, cornea 110, lens 112, iris 114, vitreous humor 116, and optic nerve 118.

Inductively-powered eye implant apparatus includes array of stimulating electrodes 120, which is connected with inner-retina neurons of retina 106 near fovea 108. Electrical cable 122 couples array 120 with processing circuit 124 in lens 112. Processing circuit 124 is electrically connected with receiver coil 126, which is surrounded in an insulative biocompatible layer. Buffer coil 128, also surrounded by an insulative biocompatible layer, is disposed outside sclera 102 and surrounds cornea 110. In operation during power transfer, buffer coil 128 and receiver coil 126 are electromagnetically coupled. Note that no cable piercing the sclera is required for power transfer to this intraocular device.

Buffer coil 128 receives a varying magnetic field by way of electromagnetic induction, and that causes current within buffer coil 128 to flow around its ring-like structure. The induced current in buffer coil 128 causes electromagnetic induction to receiver coil 126, which causes current to be induced in receiver coil 126. The current in receiver coil 126 flows to processing circuit 124, which rectifies the alternating current (AC) to direct current (DC). The resulting DC voltage and current is used for powering processing circuit 124 and electrode array 120.

Figure 1B:
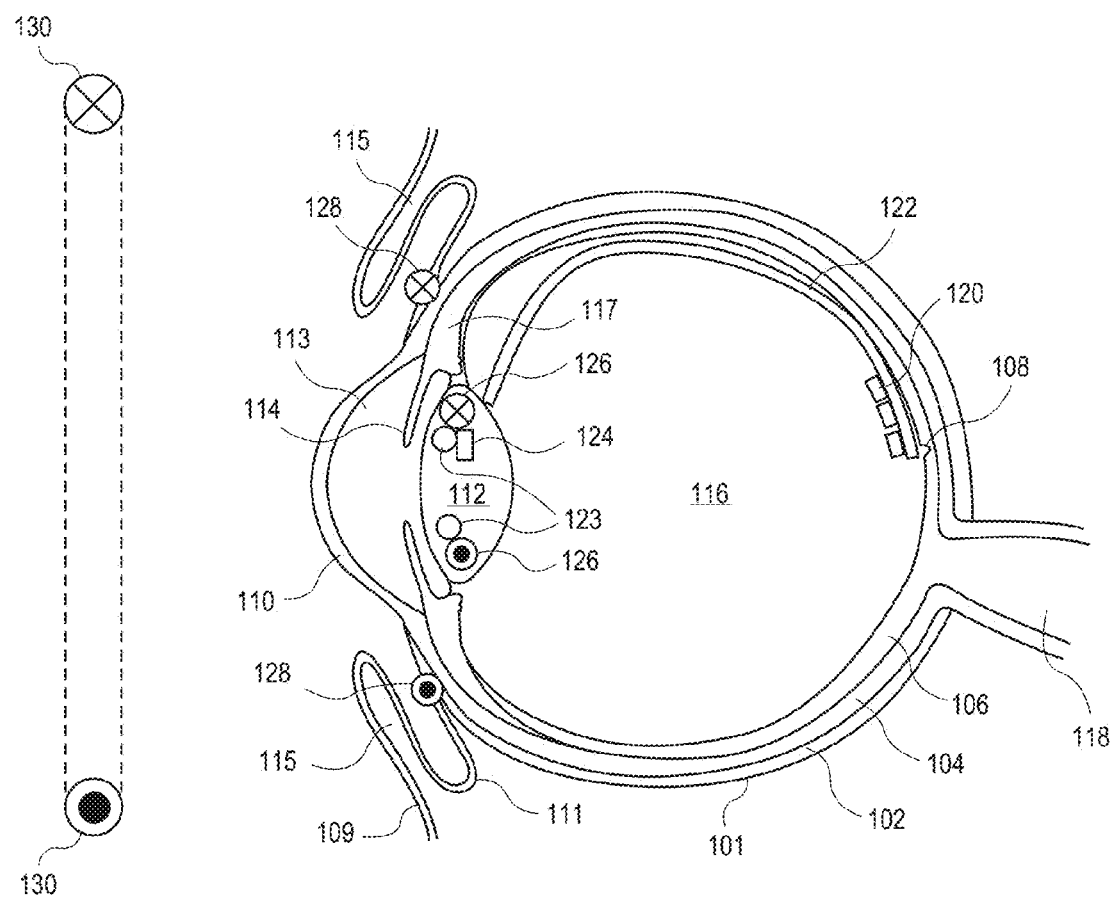
FIG. 1B is a vertical cross section of the apparatus of FIG. 1A in vivo in which the buffer coil is mounted around the cornea and under the conjunctiva of the eye.

FIG. 1B is a vertical cross section of the apparatus of FIG. 1A in vivo in which the buffer coil 128 is mounted around cornea 110 and under the conjunctiva 111 of the eye. Besides the structure of the eye enumerated earlier, other portions are shown. Episclera 101 is the outermost layer of the sclera. As seen in the bottom of the figure, skin 109 gives way to eyelid 115. Aqueous humor 113 sits within cornea 110. Ciliary body 117 holds lens 112 in place.

A cross section of transmitter coil 130 is shown with the direction of current flow depicted by an X (i.e., into the page) and a dot (i.e., out of the page). The current in transmitter coil 130 induced current in the same direction in buffer coil 128, which in turn induces current in receiver coil 126.

Receiver coil 126 is buoyantly supported by sealed, ring-shaped cavity 123. Air, nitrogen, an inert gas, or liquid with a specific gravity less than an aqueous solution is trapped within sealed cavity 123, lowering the equivalent mass of the combined receiver coil-sealed cavity structure. This can be important when using heavier metals for the receiver coil's traces, such as gold.

Figure 1C:
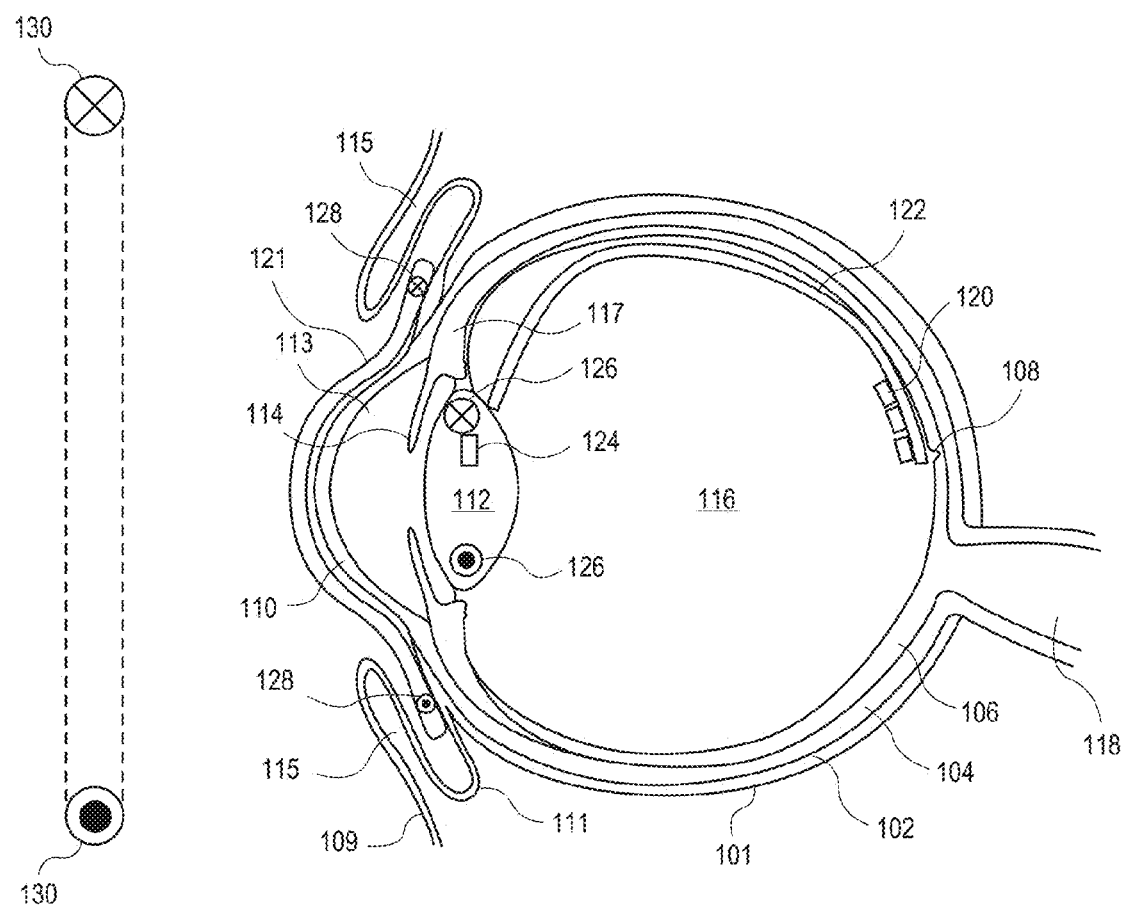
FIG. 1C is a vertical cross section of the apparatus of FIG. 1A in vivo in which the buffer coil is worn in a sclera lens.

FIG. 1C is a vertical cross section of the apparatus of FIG. 1A in vivo in which buffer coil 130 is encapsulated in sclera lens 121. Sclera lens 121 is worn by the user, kept tight by suction and meniscus forces on the eye, bearing on sclera 102. Sclera lens can be applied and removed by a patient as needed for powering the intraocular device or when efficiency is an issue. Different buffer coils can be easily tested, as no surgical procedure is necessary for the replacement of sclera lenses.

Figure 1D:
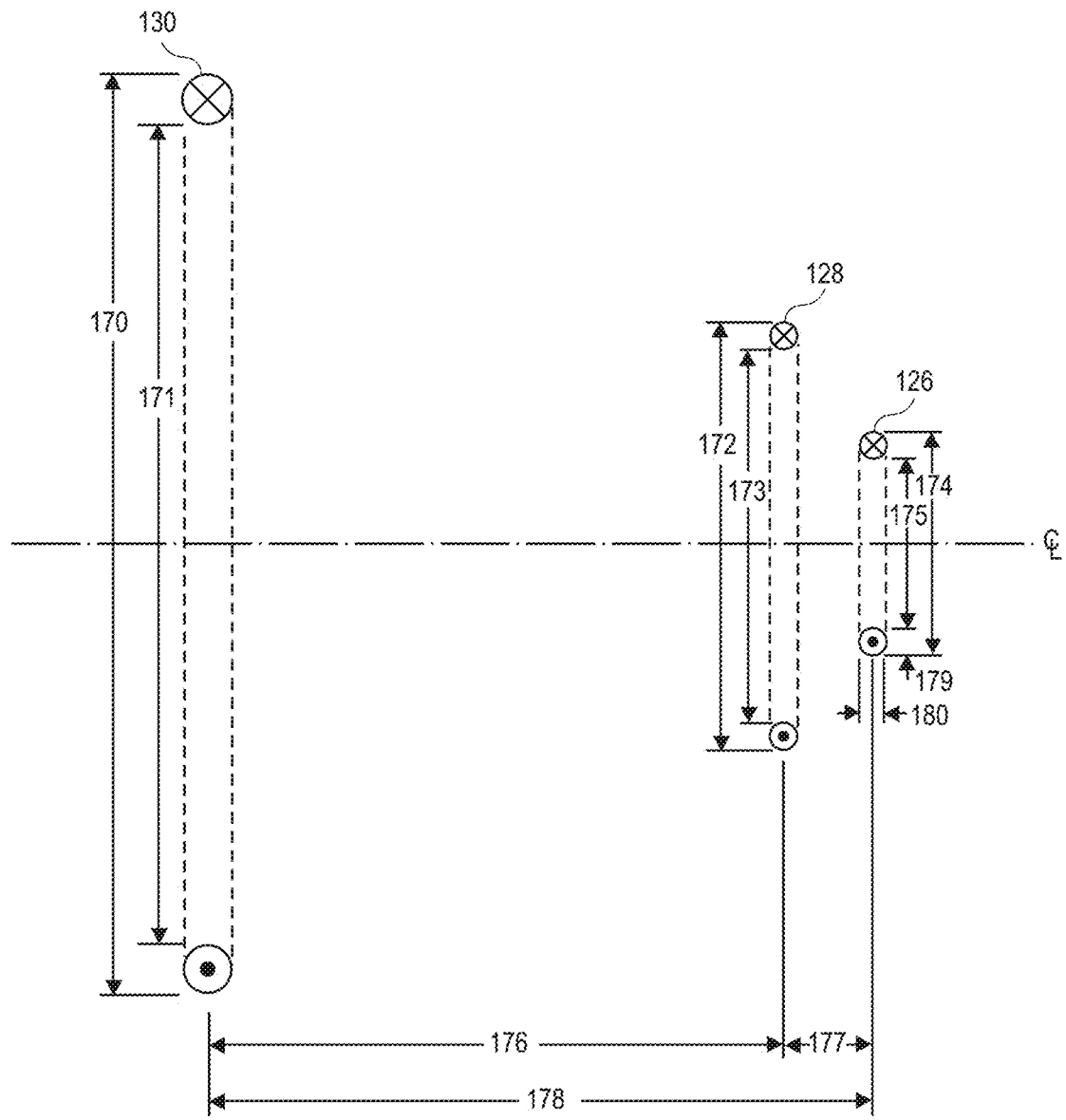
FIG. 1D is a vertical cross section of the apparatus of FIG. 1A without the eye shown for clarity of the dimensions.

FIG. 1D is a vertical cross section of the apparatus of FIG. 1A without the eye shown for clarity of the dimensions. Transmitter coil 130, buffer coil 128, and receiver coil 126 are shown to scale. Dimensions 170-180 that have been found to work for efficient power transmission at 10 MHz are shown in Table 1.

TABLE 1

| Reference Number in FIG. 1D | Description | Length |
|---|---|---|
| 170 | outer diameter of transmitter coil | 44 mm |
| 171 | inner diameter of transmitter coil | 40 mm |
| 172 | outer diameter of buffer coil | 20 mm |
| 173 | inner diameter of buffer coil | 18 mm |
| 174 | outer diameter of receiver coil | 10 mm |
| 175 | inner diameter of receiver coil | 8 mm |
| 176 | axial distance between transmitter coil and buffer coil | 25 mm |
| 177 | axial distance between buffer coil and receiver coil | 4.0 mm |

TABLE 1-continued

| Reference Number in FIG. 1D | Description | Length |
|---|---|---|
| 178 | axial distance between transmitter coil and receiver coil | 25.4 mm |
| 179 | radial thickness of receiver coil | 0.1 mm |
| 180 | axial thickness of receiver coil | 1.0 mm |

Figure 2:
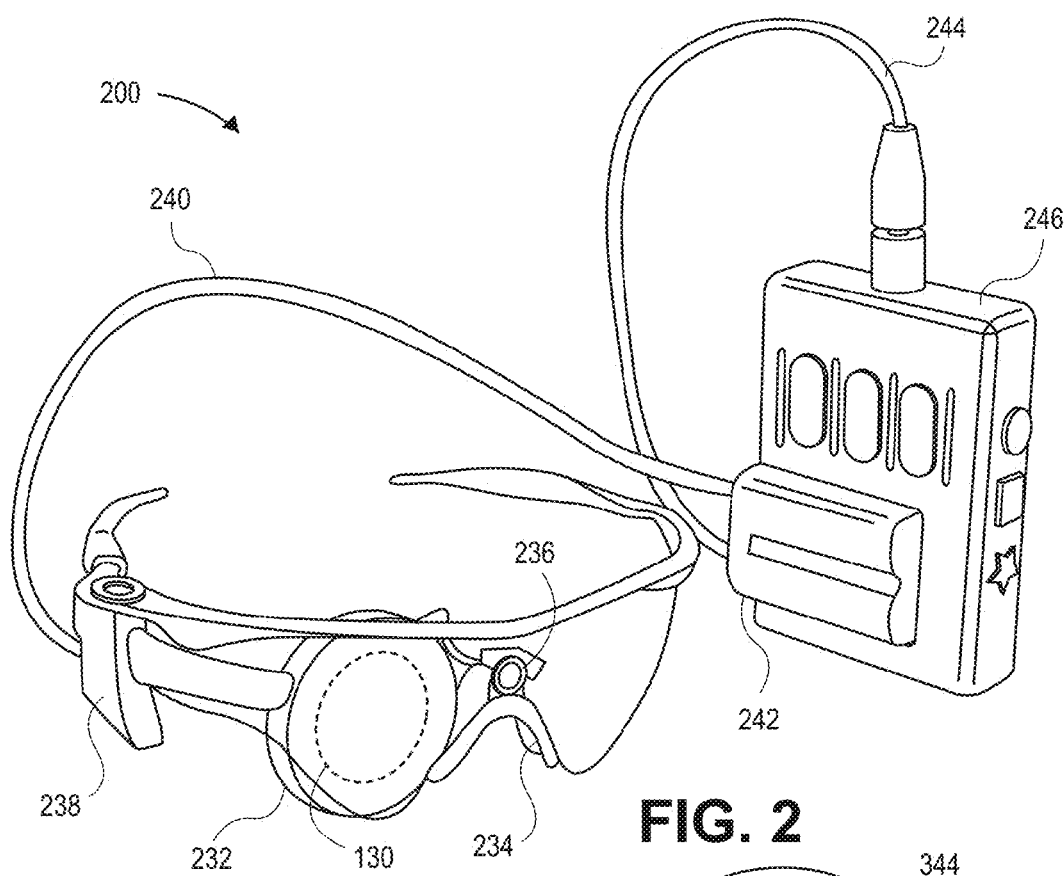
FIG. 2 illustrates a wearable transmitter assembly with the transmitter coil in front in accordance with an embodiment.

FIG. 2 illustrates a wearable transmitter assembly with the transmitter coil in front in accordance with an embodiment. This assembly can be used by patients whose buffer coil is mounted around his or her cornea, either surgically under the conjunctiva or on a sclera lens, and the receiver coil is within his or her lens capsule.

External unit 200 includes transmitter coil 130 housed in transmitter assembly 232. Transmitter assembly 232 is positioned in front of a user's eye by glasses 234. Other positioning means are envisioned.

Goggles, a helmet with a visor, spectacles, pince-nez, a monocle, binoculars, and/or an externally supported stand can hold the transmitter coil in front of the user's eyes.

Glasses 234 hold small camera 236 and video processor 238, which are connected by cable 240 to adaptor 242. Cable 244 connects another port of adaptor 242 to battery pack 246, which can be worn on a belt.

Figure 3:
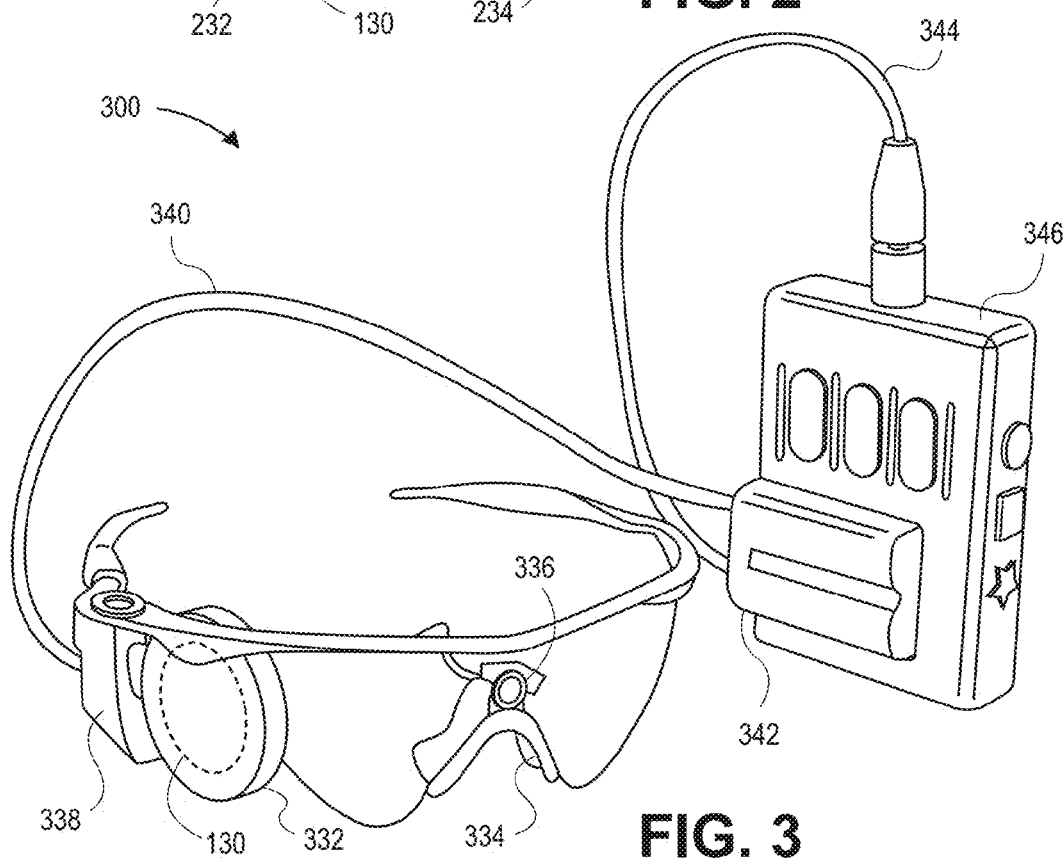
FIG. 3 illustrates a wearable transmitter assembly with the transmitter coil on the side in accordance with an embodiment.

FIG. 3 illustrates a wearable transmitter assembly with the transmitter coil on the side in accordance with an embodiment. This assembly can be used by patients whose buffer coil is affixed to a side of the eye external to the sclera, on the episclera, and their receiver coil is mounted within a vitreous body of the eye within the sclera, to the inside side of the eyeball.

External unit 300 includes transmitter coil 130 housed in transmitter assembly 332. Transmitter assembly 332 is positioned to the side of a user's eye by glasses 334. Other positioning means, such as those disclosed above, are envisioned.

Glasses 334 hold small camera 336 and video processor 338, which are connected by cable 340 to adaptor 342. Cable 344 connects another port of adaptor 342 to battery pack 346, which can be worn on a belt.

A lens capsule is a prime location for mounting a receiver coil. A small incision may be made if the receiver coil is fashioned so that it is substantially wider axially than radially and resilient. The receiver coil can then be pinched to transport it through the small incision.

"Substantially wider axially than radially" includes ratios of axial width to radial height of 4:1, 5:1, 6:1, 7:1, 8:1, 9:1, 10:1, 15:1, 20:1, 25:1, 50:1, 100:1, and other ratios.

Figure 4A:
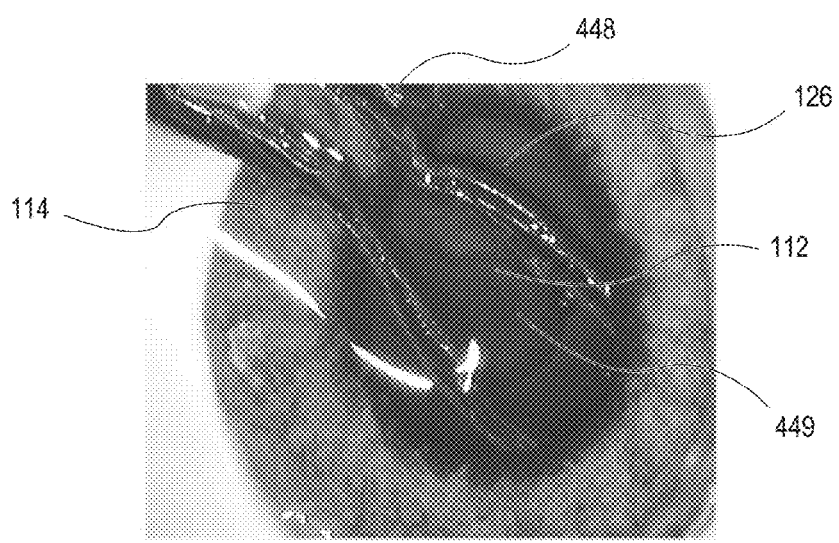
FIG. 4A is a picture of pinching and inserting into a lens capsule a receiver coil in accordance with an embodiment.

FIG. 4A is a picture of pinching and inserting into a lens capsule a receiver coil in accordance with an embodiment. Lens 112 of an porcine eye is surrounded by iris 114. Incision 449 is made in lens 112. Receiver coil 126 has been resiliently pinched to an oblong shape by tweezers 448 and is inserted through incision 449. After receiver coil 126 is safely inside the lens capsule, tweezers 448 are drawn back and the coil is left to regain its shape within lens 112.

Figure 4B:
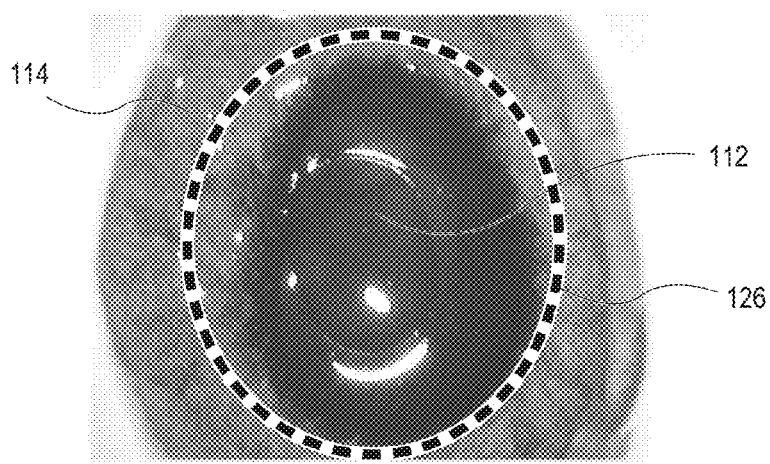
FIG. 4B is an annotated picture of the receiver coil of FIG. 4A springing to full diameter within the lens capsule.

FIG. 4B is an annotated picture of the receiver coil of FIG. 4A springing to full diameter within the lens capsule. The dotted line shows an ideal springback shape of receiver coil 126.

Figure 4C:
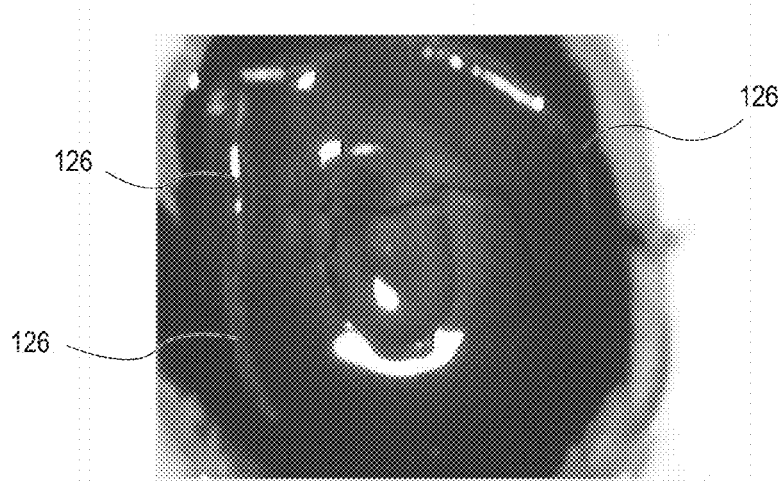
FIG. 4C is a picture of the lens capsule of FIG. 4B with the eye's iris removed for clarity.

FIG. 4C is a picture of the lens capsule of FIG. 4B with the eye's iris removed for clarity. Note that receiver coil 126 has sprung to a wide diameter, filling up the lens capsule. Although it is not perfectly circular after springing back, it is not necessary for the power transmitting coil to be perfectly circular. Various shapes can work because the system is robust.

To fit inside a lens, it has been found that a circular receiver coil with an outer diameter equal to or less than 10 mm works well. The minimum inner diameter of the receiver coil is thought to be equal to or greater than 6 mm. An axial thickness of equal to or less than 1 mm is preferred for a 10 mm diameter receiver coil.

From an axial direction, the receiver coil of the exemplary embodiment is circular. However different shapes, including ovals and other rounded shapes, polygons, and hybrid rounded-straight sided shapes are envisioned. The method of manufacturing described herein allow many opportunities for geometric shape optimizing.

An "oval" shape includes an ellipse or egg shape. For example, a buffer coil can be oval and have an outer minor axis of about 19 millimeters and an outer major axis of about 24 millimeters. These dimensions have been found to be efficient when the major axis is placed horizontally because eyes can rotate more horizontally than vertically.

A "polygon" shape includes closed forms with straight edges, including a triangle, quadrilateral, pentagon, hexagon, etc.

Figure 5:
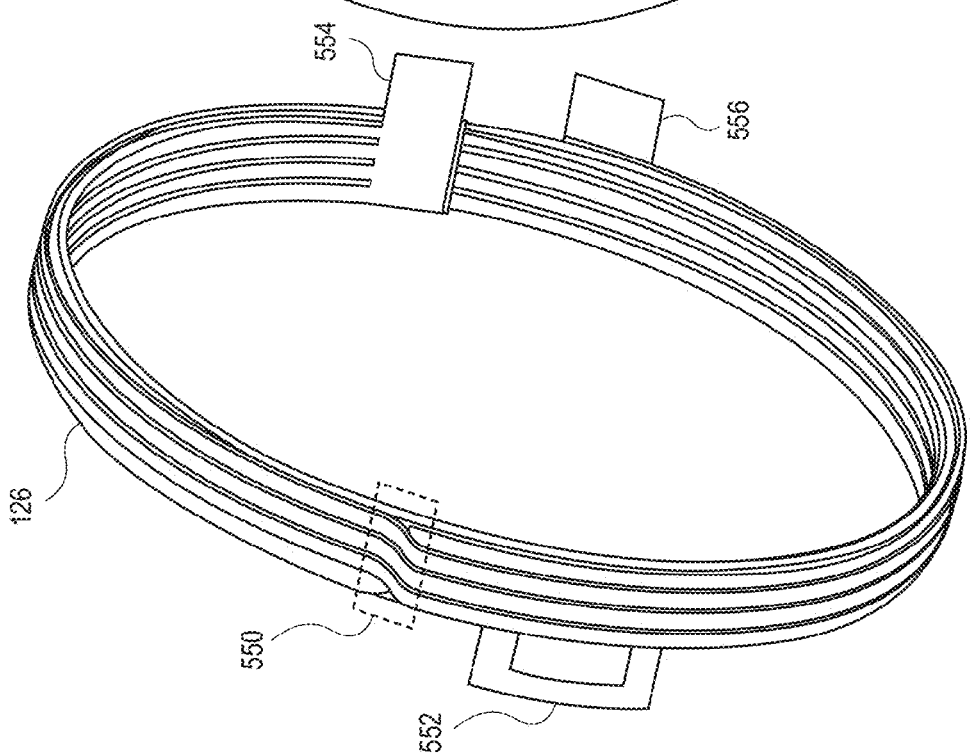
FIG. 5 illustrates a receiver coil in accordance with an embodiment.

FIG. 5 illustrates a receiver coil in accordance with an embodiment. Receiver coil 126 includes conductive pads 554 and 556, which connect all of the traces at each end. Pads 554 and 556 can be electrically connected, by soldering or other means, to a processing circuit. Region 550 shows a shifting region of the traces that shifts an (axially) internal trace to the outside. This can be helpful in spreading the proximity effect among the traces, thereby lowering the total proximity effect of the receiver coil.

U-shaped region 552 connects traces wrapping one way around the receiver coil to those wrapping an opposite direction around the coil. Like the regions shown by pad 554, all of the traces may be connected at the U-shaped region end.

Figure 6:
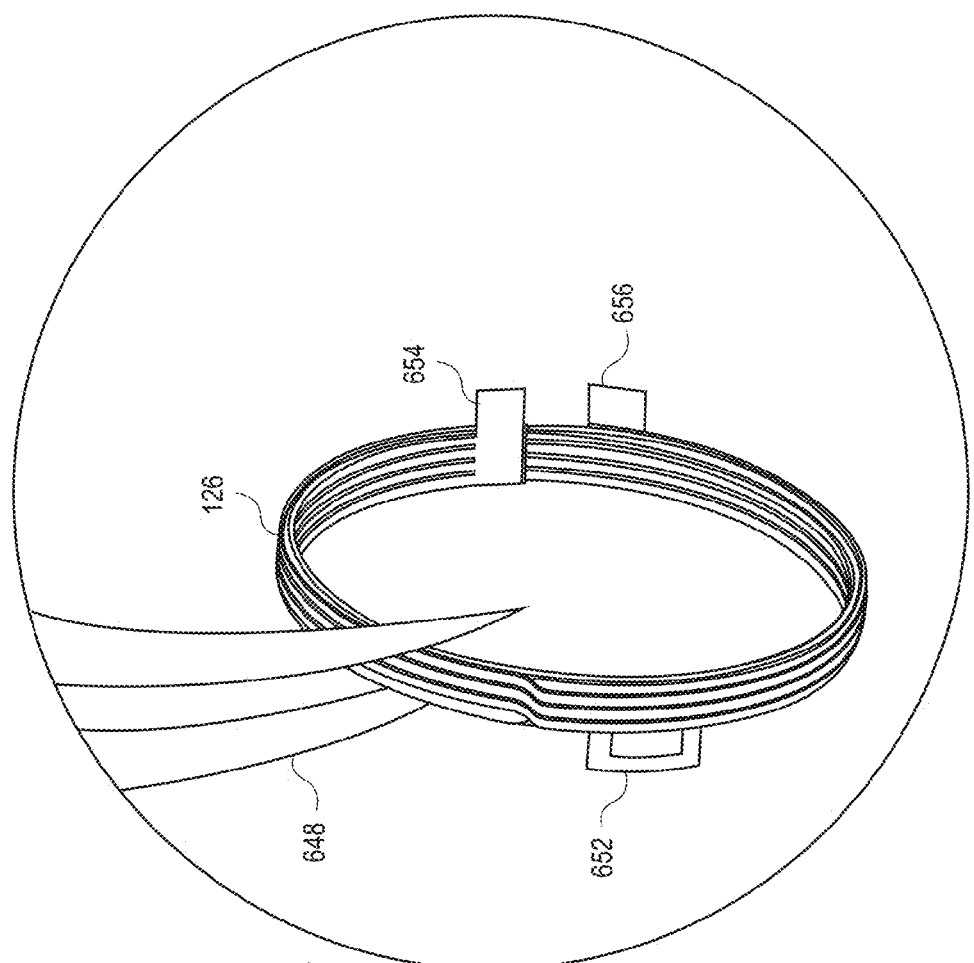
FIG. 6 illustrates a receiver coil held by tweezers in accordance with an embodiment.

FIG. 6 illustrates a receiver coil held by tweezers in accordance with an embodiment. Receiver coil 126 includes conductive pads 654 and 656, which connect all of the traces at each end. U-shaped section 652 connects traces wrapping one way around the receiver coil to those wrapping the opposite direction. Tweezers 648 are shown for scale.

Manufacturing a coil using micromachining techniques on a flat surface has its advantages. However, with parallel traces on a two-dimensional sheet, it is difficult to spread the proximity effect. Microelectromechanical systems (MEMS) technology is used to fashion a MEMS foil coil design with litz wire-like properties. Litz wire-like properties are achieved by shifting traces so that when they are folded and coiled into a ring, the traces trade axial positions in the ring.

FIGS. 7-11 illustrates a ribbon of etched traces on a flat surface with applicable cross sections in accordance with a method for manufacturing a coil with litz wire-like properties. Ribbon 726 has been manufactured with conductive metal traces 766, 768, and seven others. The traces shift in three discrete areas along the length of the ribbon. Ribbon 726 is to be folded along longitudinal fold lines (i.e., creases) 761 and 763. Creases 761 and 763, which may or may not be simply lines, longitudinally separate ribbon 726 into three regions or folds: fold 760, fold 762, and fold 764.

There are four traces per fold. Trace 766 starts at the upper left of fold 760 and snakes down to the opposite (axial, when rolled up) side of fold 760 on the right. Meanwhile, trace 768 starts at the second position in the upper left of fold 760 and snakes down to cross crease 761 and end up in the upper part of fold 762 on the right. Trace 768 crosses fold line 761 at a point between cross sections 10-10 and 11-11.

Figure 12:
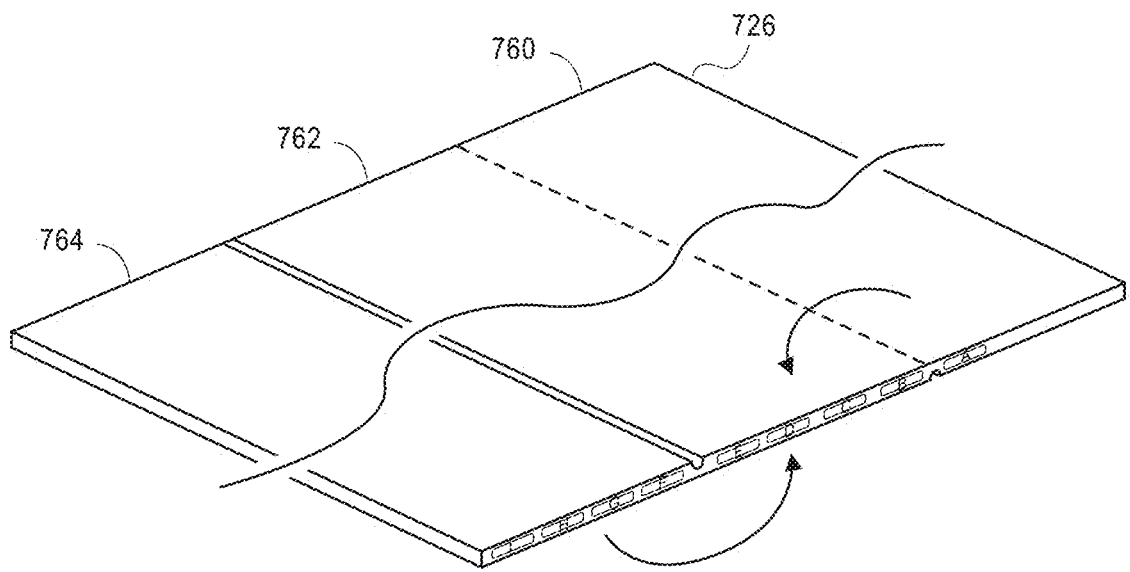
FIG. 12 illustrates folding a ribbon of etched traces in accordance with an embodiment.
Figure 13:
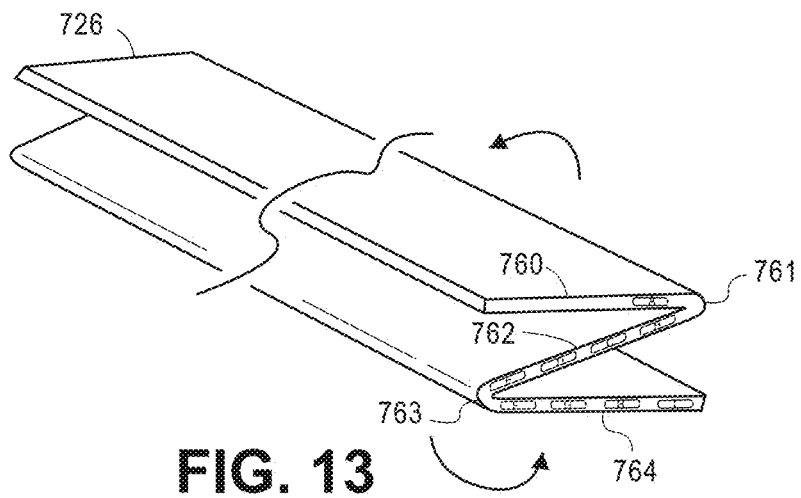
FIG. 13 illustrates further folding a ribbon of etched traces in accordance with an embodiment.
Figure 14:
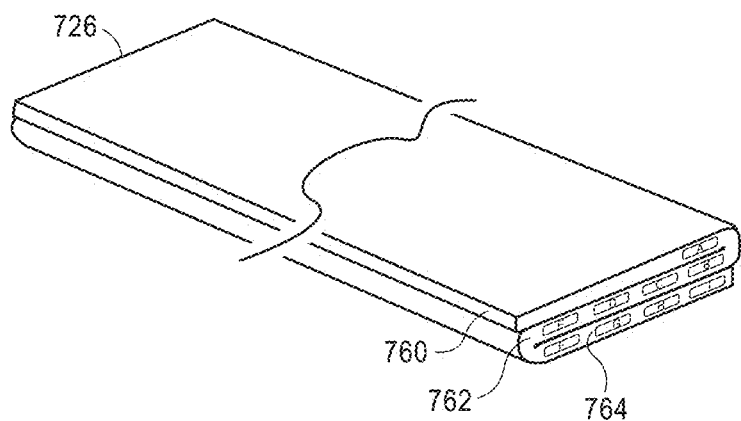
FIG. 14 illustrates a fully (longitudinally) folded ribbon of stacked etched traces in accordance with an embodiment.

FIGS. 12-14 illustrates folding a ribbon of etched traces to stack them on top of each other in accordance with an embodiment. In FIG. 12, ribbon 726 is flat with folds 760, 762, and 764 in the same plane. In FIG. 13, fold 760 is folded along crease 761 over fold 762. Fold 764 is folded along crease 763 under fold 762. In FIG. 14, fold 760 and its embedded conductors are fully stacked on top of fold 762 and its conductors, which are stacked on top of fold 764 and its conductors. The folded ribbon is then wound into a coil.

Figure 15:
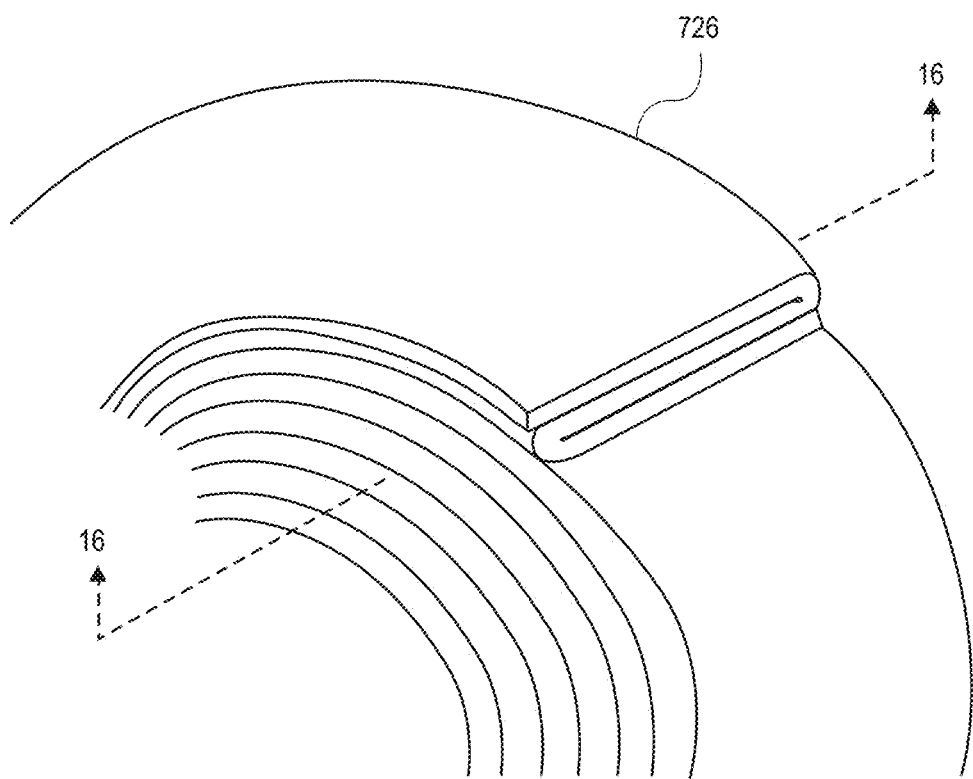
FIG. 15 illustrates a wound coil of etched traces in accordance with an embodiment.

FIG. 15 illustrates a wound coil of etched traces in accordance with an embodiment. Folded and wound ribbon 726 is shown with each of its three folds stacked atop one another and then coiled.

FIG. 16 is a cross section of a wound coil of stacked etched traces, along with additional stacks of traces from a U-turn, in accordance with an embodiment. The bottom half of the figure shows folds 760, 762, and 764 as they would be stacked when wound into a coil multiple times around. Note that the conductor traces shift their axial (i.e., left-right in the figure) positions. This sharing of the (axial) outside positions allows the traces to share the proximity effect, which causes the current in the traces to flow most freely in the outer positions.

Above the U-turn are folds 1660, 1662, and 1664. These folds started out on the same flat sheet as folds 760, 762, 764, and have been folded over each other like folds 760, 762, and 764. However, they are folded back to go in an opposite direction over folds 760, 762, and 764. The resulting stack of folds and U-turned traces is a stack of a total of 24 layers. That is, a cross section of the ring has 24 layers. This is merely one embodiment. Coils with 6, 7, 8, 9, 10, 15, 20, and more traces per fold are also envisioned as well as coils with more or fewer wrap arounds. The number of stacks is dependent on the number of times that the ribbon is coiled upon itself, which itself is dictated by the target diameter of the final coil (and length of the flat ribbon).

The U-turn of the conductors is enabled by a U-shaped region in the traces when they are initially micromachined on a flat surface. This U-shaped region, and overall micromachining techniques, are discussed below.

FIG. 17 illustrates a flat sheet on a substrate in accordance with an embodiment. Silicon wafer substrate 1770 supports biocompatible electrical insulator 1772. Cross section 18-18 is shown in FIG. 18. Biocompatible layer/insulator can include material selected from the group consisting of implantable epoxy, liquid crystal polymer (LCP), parylene C, silicone, and other biocompatible materials.

FIG. 19 illustrates etched conductor traces in accordance with an embodiment. Conductor traces 1974 have been applied atop electrical insulator 1772. Cross section 20-20 is shown in FIG. 20. Conductor traces are manufactured by depositing a thin metal layer on top of electrical insulator 1772 and etching away the spaces between the traces. Other micromachine methods are contemplated. Note that there are three conductors on each side.

FIG. 21 illustrates embedded conductor traces in accordance with an embodiment. More electrical insulator 2177 has been deposited over conductor traces 1974 to embed them within electrical insulator 2177, forming a biocompatible layer over the conductors.

To "embed" electrical traces in an insulator includes covering them with insulator sufficient to prevent short circuits at nominal voltages, or otherwise known in the art.

Creases 2176 have been pre-formed in the material by etching away electrical insulator in longitudinal lengths. FIG. 22 shows cross section 22-22.

U-shaped section 2152 connects both sides of conductors to each other. In the exemplary embodiment, it is formed so that all conductor traces are connected. The lengths of conductor that project from it do so in a common direction (i.e., up in the figure).

Figure 23:
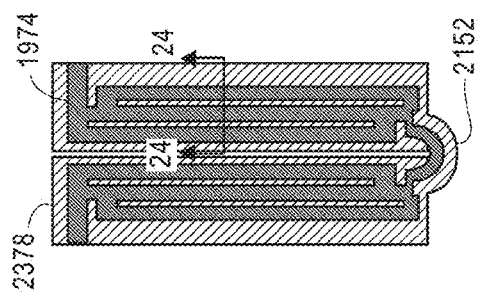
FIG. 23 illustrates a ribbon of embedded traces in accordance with an embodiment.

FIG. 23 illustrates a ribbon of embedded traces in accordance with an embodiment. Ribbon 2378 has been created by peeling electrical insulator 2177, with its embedded conductor traces 1974, from the flat substrate.

Figure 24:
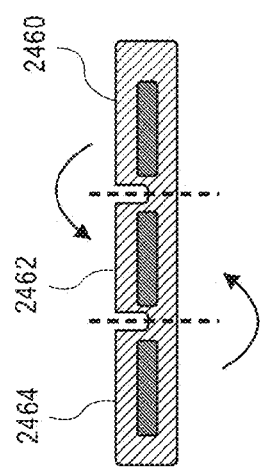
FIG. 24 is cross section 24-24 of FIG. 23.

FIG. 24 shows cross section 24-24. Longitudinal depressions have been created by further etching in order to facilitate longitudinal folding along the creases. Fold 2460 is folded over middle fold 2462, and fold 2464 is folded under fold 2462. This stacks the traces in three layers.

Figure 25:
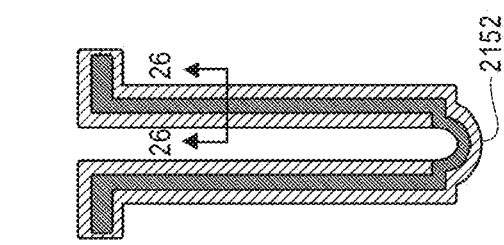
FIG. 25 illustrates stacked traces in accordance with an embodiment.
Figure 26:
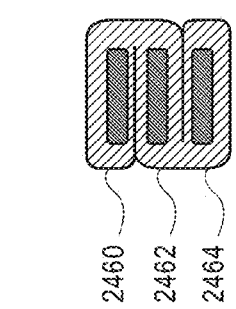
FIG. 26 is cross section 26-26 of FIG. 25.

FIG. 25 illustrates stacked traces in accordance with an embodiment. This is a result of the folding. FIG. 26 shows cross section 26-26. Folds 2460, 2462, and 2464 are stacked atop one another. This embodiment shows single conductors on each fold for simplicity in illustration. Other numbers of conductors on each layer are envisioned, such as those shown in FIG. 14, etc.

Figure 27:
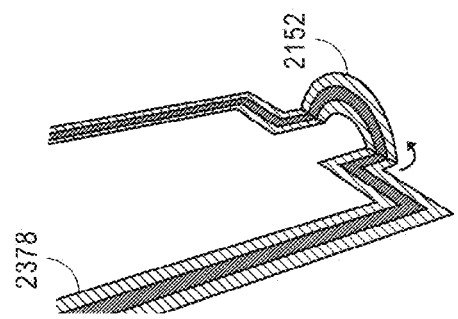
FIG. 27 illustrates folding up a U-section of a ribbon in accordance with an embodiment.

FIG. 27 illustrates folding up a U-section of a ribbon in accordance with an embodiment. Ribbon 2378 is folded such that U-section 2152 is perpendicular to the rest of the ribbon.

Figure 28:
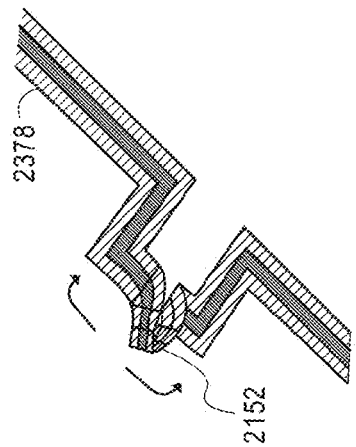
FIG. 28 illustrates folding a U-section of a ribbon in accordance with an embodiment.

FIG. 28 illustrates folding U-section 2152 of ribbon 2378 in half such that the lengths of conductor that once projected in the same direction (i.e., up in FIG. 27) now project in opposite directions from one another. The result is an extra long ribbon of conductors.

In some embodiments, the U-section does not connect all of the conductor traces to one another but keeps them separately attached to respective conductor traces on the other side of the U-section.

Figure 29:
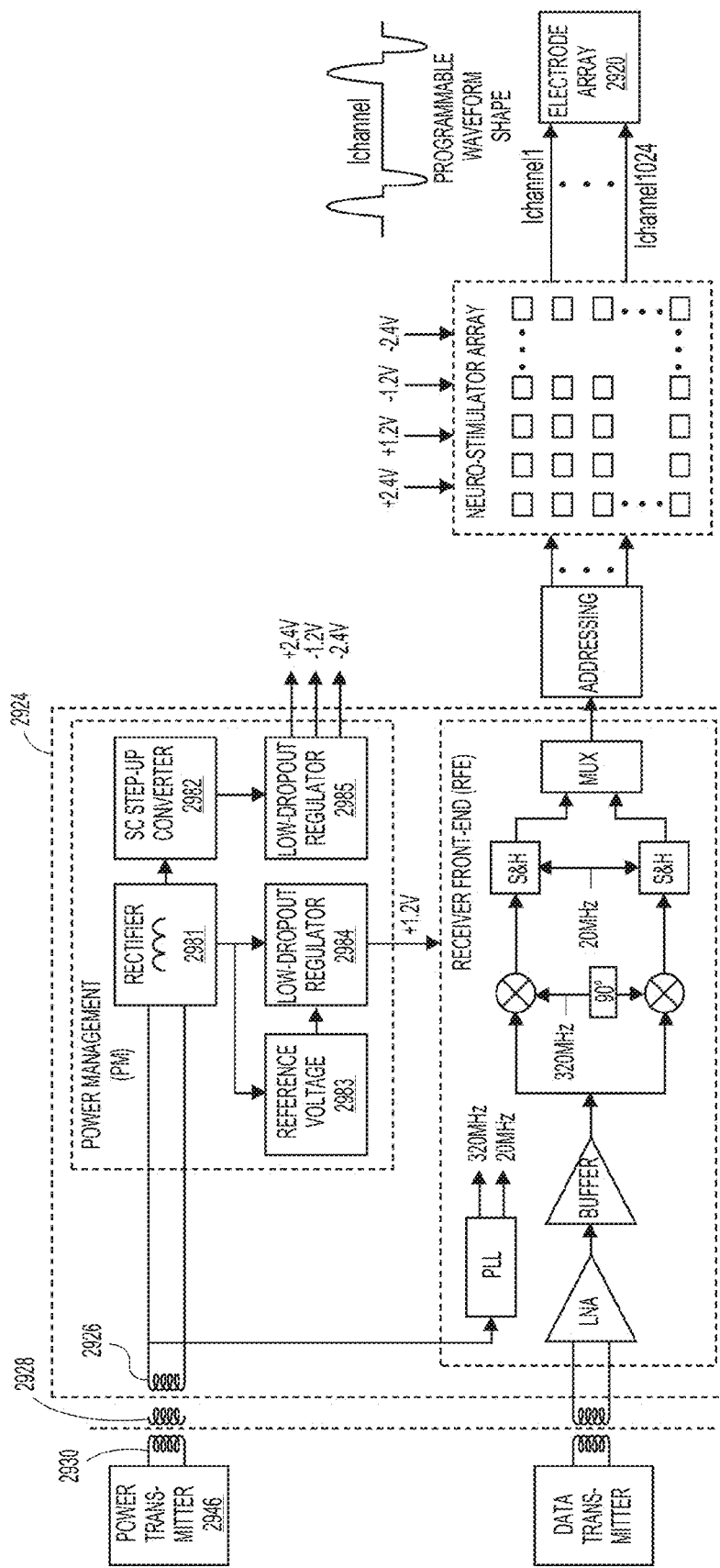
FIG. 29 illustrates an eye implant power and data transfer architecture in accordance with an embodiment.

FIG. 29 illustrates an eye implant power and data transfer architecture in accordance with an embodiment. Power transmitter 2946 energizes transmitter coil 2930, which electromagnetically couples with buffer coil 2928. Buffer coil 2928 electromagnetically couples with receiver coil 2926 in intraocular system 2924.

Within intraocular system 2924, output from receiver coil 2926 is connected with rectifier 2981, which rectifies the induced, sinusoidal AC current. The rectified current is sent to reference voltage module 2983 and low-dropout regulator 2984. Low-dropout regulator 2984 supplies +1.2 volts (V) to a receiver front end. Rectified current is also sent to SC step-up converter 2982, which supplies low-dropout regulator 2985 with power. Low-dropout regulator 2985 supplies +2.4 V, −1.2 V, and −2.4 V predominately to a neuro-stimulator array. The neuro-stimulator array is intimately connected to electrode array 2920, which is connected with inner-retina neurons of the eye.

Figure 30:
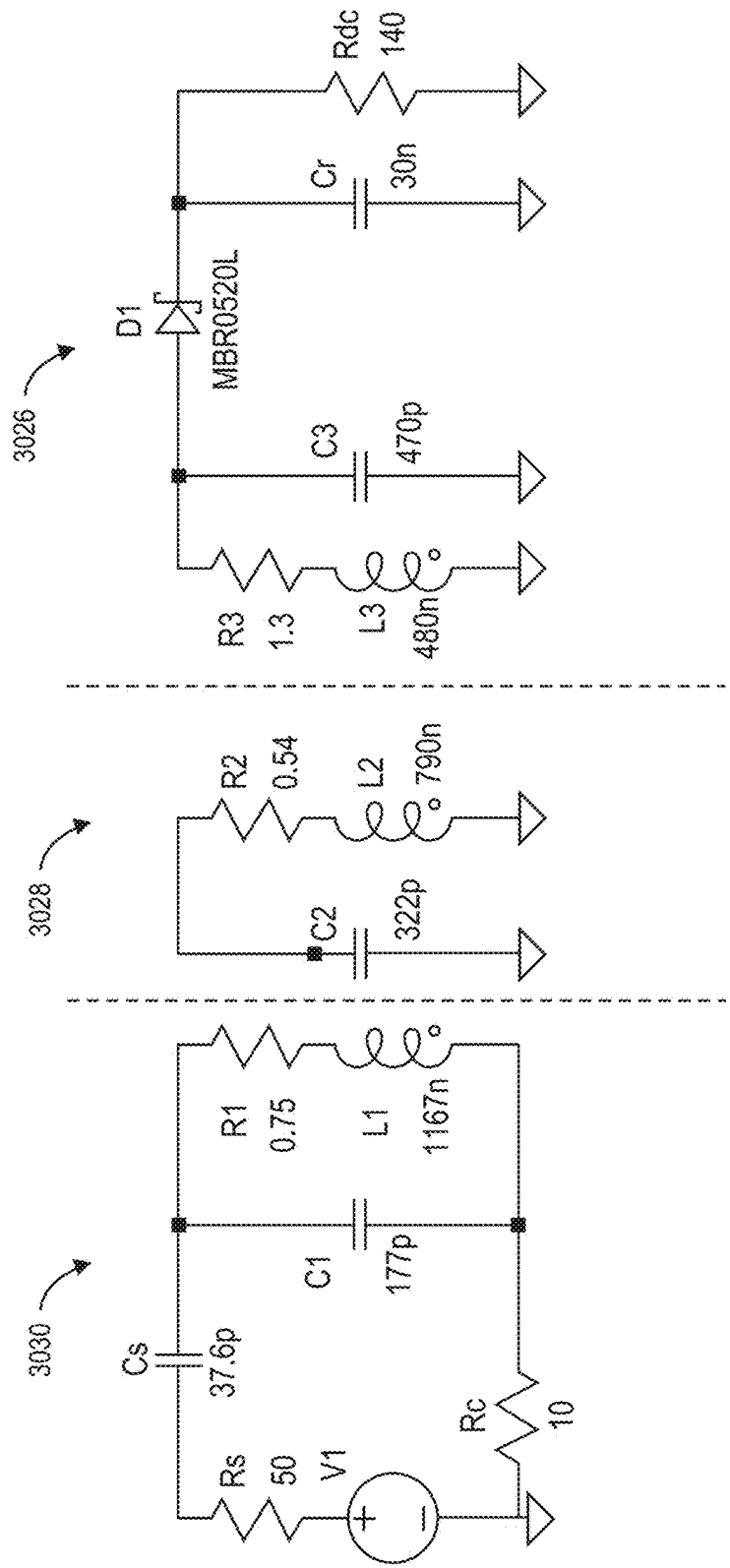
FIG. 30 illustrates modeled circuit values of a three-coil system for efficiency determinations in accordance with an embodiment.

FIG. 30 illustrates modeled circuit values of a three-coil system for efficiency determinations in accordance with an embodiment.

Transmitter 3030 is modeled with voltage supply V1, a resistor Rs of 50Ω (ohms) in series with a capacitor Cs of 37.6 picofarads (pF). They are connected in parallel with grounded resistor Rc of 10Ω with capacitor C1 of 177 pF and a coil, modeled with resistor R1 of 0.75Ω and an inductor L1 of 1167 nH (nano Henries).

Buffer coil 3028 is modeled with grounded capacitor C2 of 322 pF connected in series to a coil, modeled as resistor R2 of 0.54Ω and an inductor L2 of 790 nH.

Receiver 3026 is modeled with a grounded coil, R3 of 1.3Ω and an inductor L3 of 480 nH. They are connected to grounded capacitor C3 of 470 pF, then to the anode of Schottky diode D1 (MBR0520L). The cathode of Schottky diode D1 is connected with grounded capacitor Cr of 30 nF and grounded resistor Rdc of 140Ω.

Using this model, with equivalent loads of 1.9 V and a power consumption of 25.8 mW, efficiency of the 3-coil system was calculated at 35.9%. This is in comparison to a 2-coil efficiency of 0.7%.

As the eyeball and thus buffer coil and receiver coil are rotated from 0° to 30°, efficiencies falls off from 35.9% at 0° to the high teen percentages at 30°. Thus, even at the maximum angle that an eye can rotate, efficiency is better than in an equivalent 2-coil system.

Figure 31:
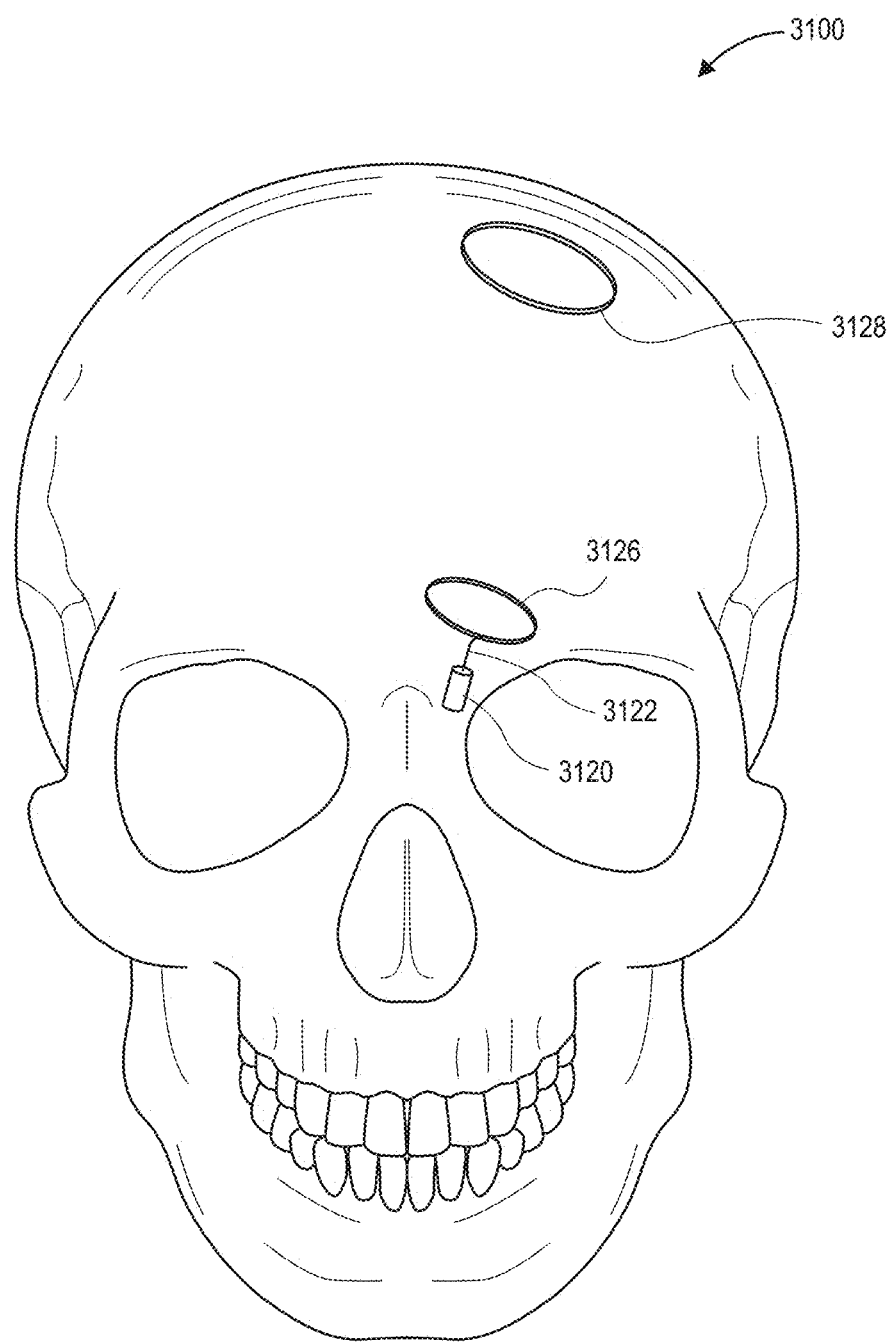
FIG. 31 illustrates a brain implant in accordance with an embodiment.

FIG. 31 illustrates a brain implant in accordance with an embodiment. Deep brain stimulation (DBS) requires an implant to be deeply buried within the brain. This is a candidate for the three-coil system. A 100-channel Utah electrode array is connected with a signal processing application-specific integrated circuit (ASIC), which can receive power through a thin-film fabricated gold-on-polyimide power coil.

By putting the transmitter coil close to the outer skin of the head and a receiving coil deep inside the skull, efficiency can be improved by introducing a buffer coil.

In system 3100, buffer coil 3128 is implanted just inside the skull cavity while receiver coil 3126 is deep within the brain. Receiver coil 3126 is connected by cable 3122 to electrode 3120. When a transmitter coil inductively couples with buffer coil 3128, efficiency is improved in transferring energy to receiver coil 3126.

Figure 32:
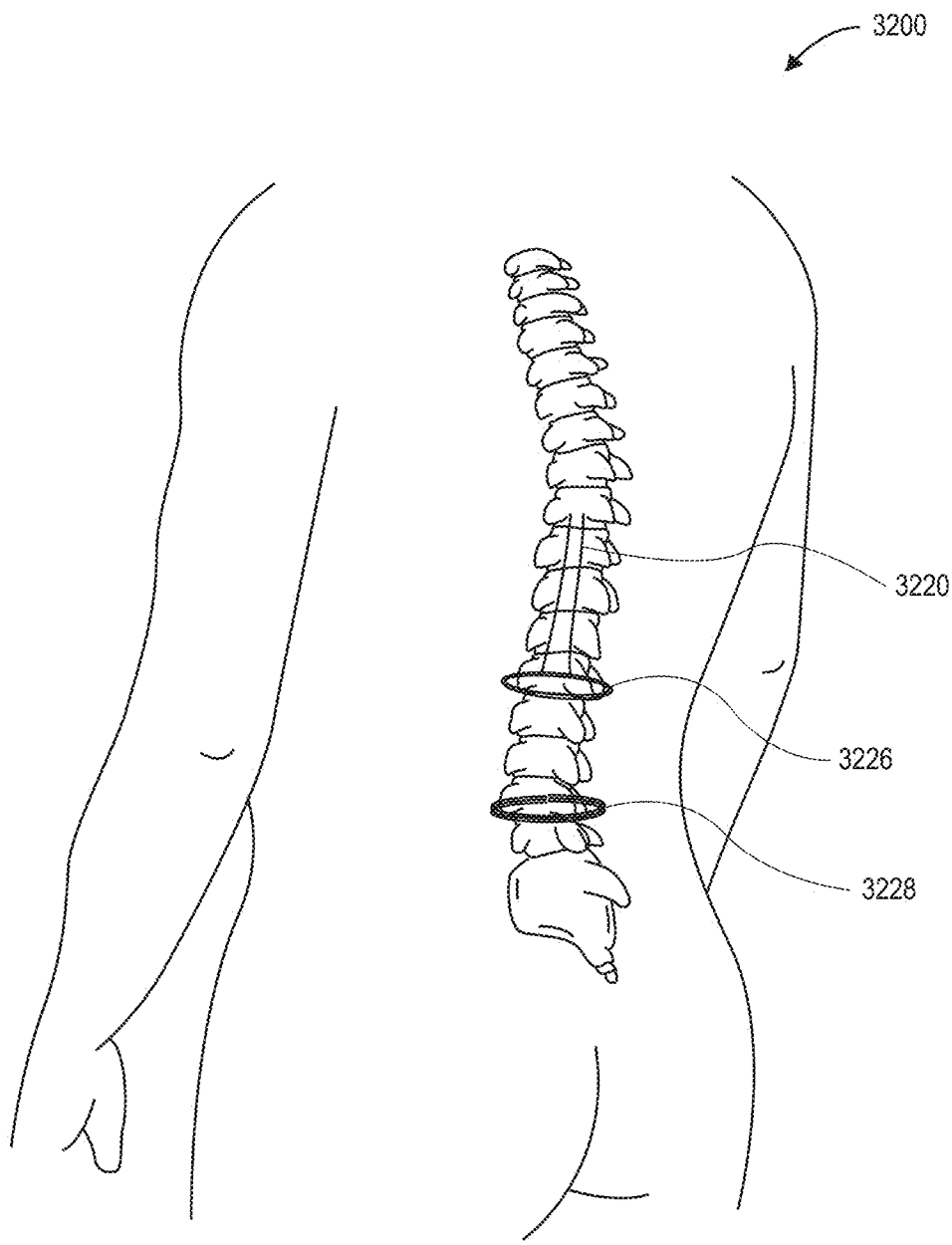
FIG. 32 illustrates a spinal implant in accordance with an embodiment.

FIG. 32 illustrates a spinal implant in accordance with an embodiment. In system 3200, electrodes 3220 are connected with receiver coil 3226. Buffer coil 3228 allows a more efficient transfer of power from an external transmitting coil to receiver coil 3226.

Figure 33:
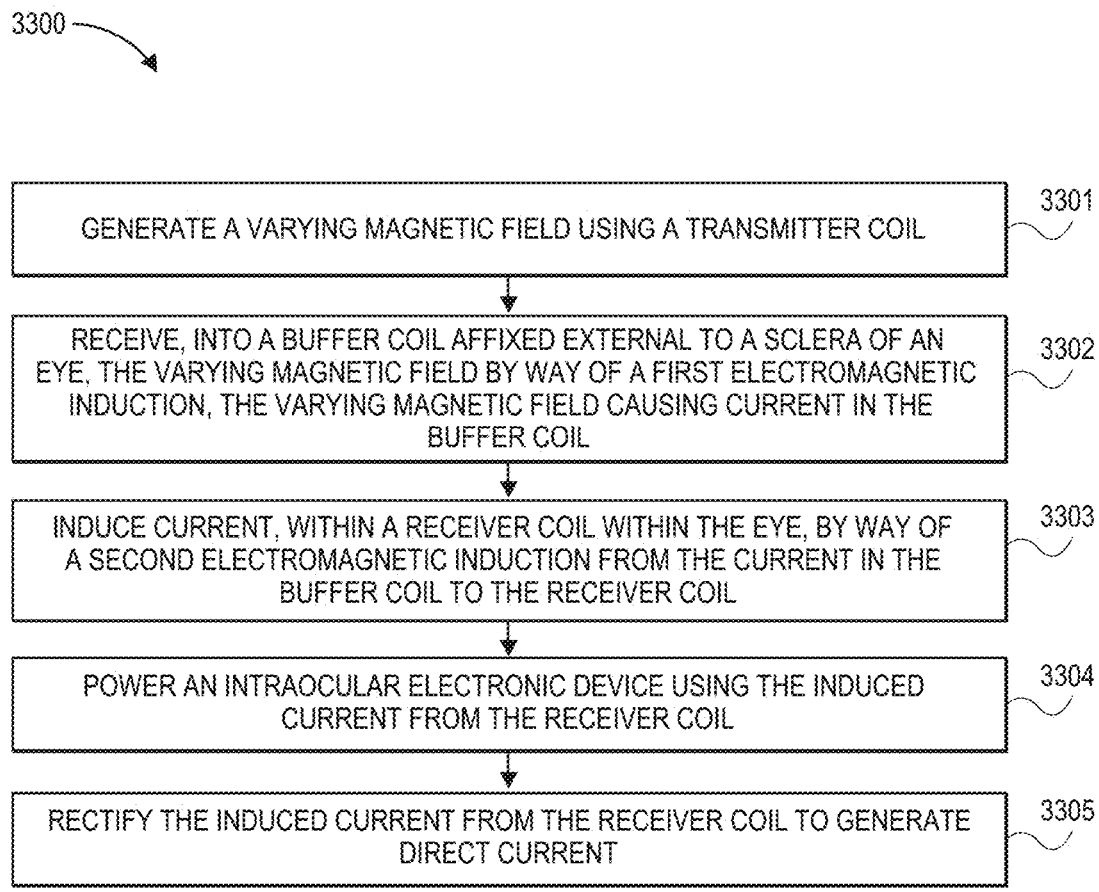
FIG. 33 is a flowchart of a process in accordance with an embodiment.

FIG. 33 is a flowchart of a process in accordance with an embodiment. Process 3300 has several operations. In operation 3301, a varying magnetic field is generated using a transmitter coil. In operation 3302, the varying magnetic field is received, into a buffer coil affixed external to a sclera of an eye, by way of a first electromagnetic induction, the varying magnetic field causing current in the buffer coil. In operation 3303, current is induced, within a receiver coil within the eye, by way of a second electromagnetic induction from the current in the buffer coil to the receiver coil. In operation 3304, an intraocular electronic device is powered using the induced current from the receiver coil. In operation 3305, the induced current from the receiver coil is optionally rectified to generate direct current.

Figure 34:
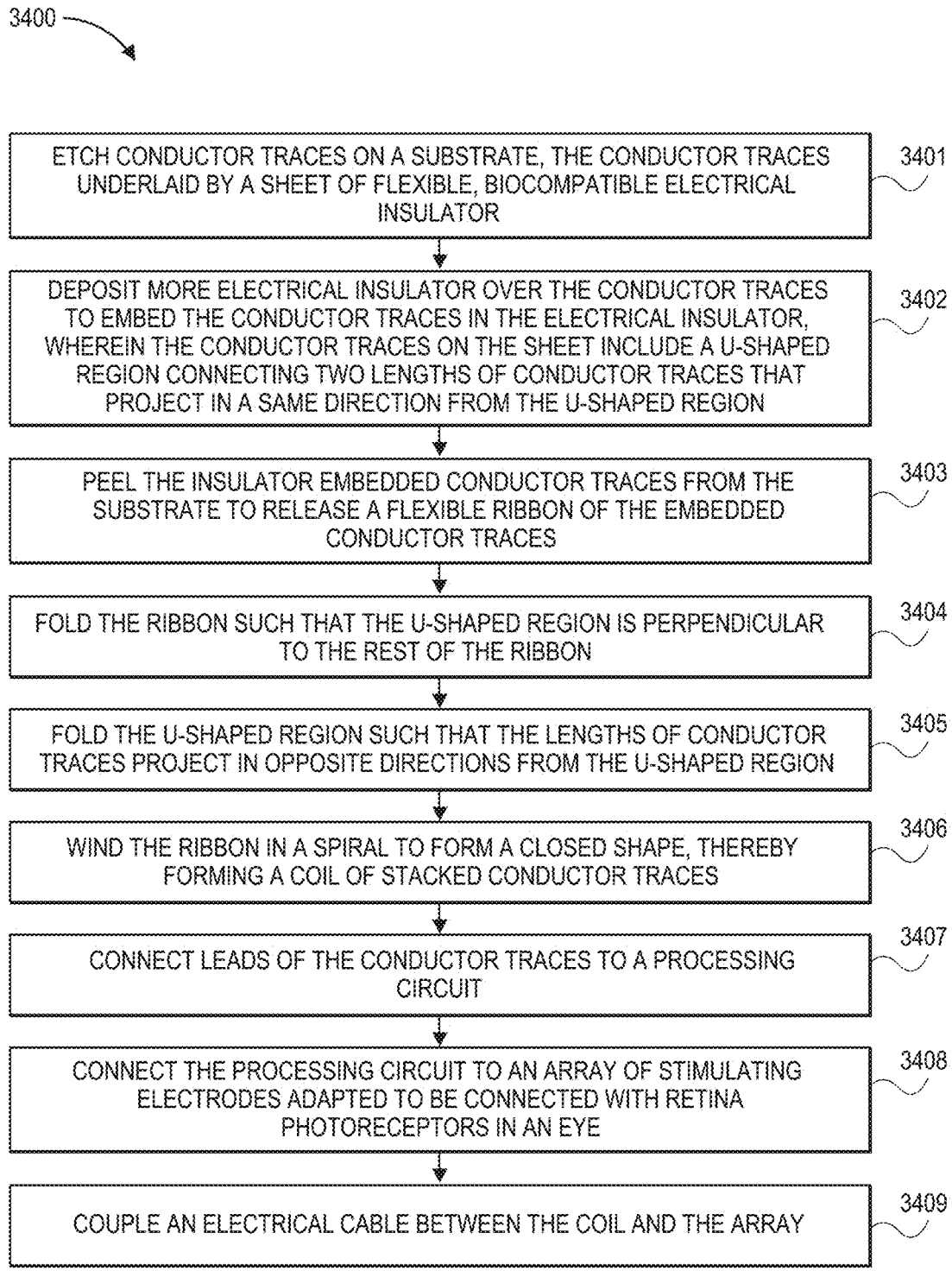
FIG. 34 is a flowchart of a process in accordance with an embodiment.

FIG. 34 is a flowchart of a process in accordance with an embodiment. Process 3400 has several operations. In operation 3401, conductor traces are etched on a substrate, the conductor traces underlaid by a sheet of flexible, biocompatible electrical insulator. In operation 3402, more electrical insulator is deposited over the conductor traces to embed the conductor traces in the electrical insulator, where the conductor traces on the sheet include a U-shaped region connecting two lengths of conductor traces that project in a same direction from the U-shaped region. In operation 3403, the insulator embedded conductor traces are peeled from the substrate to release a flexible ribbon of the embedded conductor traces. In operation 3404, the ribbon is folded such that the U-shaped region is perpendicular to the rest of the ribbon. In operation 3405, the U-shaped region is folded such that the lengths of conductor traces project in opposite directions from the U-shaped region. In operation 3406, the ribbon is round in a spiral to form a closed shape, thereby forming a coil of stacked conductor traces. In operation 3407, leads or pads of the conductor traces are connected to a processing circuit. In operation 3408, the processing circuit is connected to an array of stimulating electrodes adapted to be connected with inner-retina neurons in an eye. In operation 3409, an electrical cable is coupled between the coil and the array.

The invention has been described with reference to various specific and illustrative embodiments. However, it should be understood that many variations and modifications may be made while remaining within the spirit and scope of the following claims.

What is claimed is:

1. A method of efficiently receiving power inside an eye lens for an intraocular electronic device, the method comprising:
   receiving, into a buffer coil affixed external to a sclera of an eye and surrounding a cornea of the eye, a varying magnetic field by way of a first electromagnetic induction, the varying magnetic field causing a first current in the buffer coil;
   inducing a second current, within a receiver coil within a lens capsule of the eye, by way of a second electromagnetic induction from the first current in the buffer coil to the receiver coil, the receiver coil having been produced by winding a ribbon of embedded conductor traces into a spiral; and
   powering an intraocular electronic device using the second current from the receiver coil within the lens capsule.

2. The method of claim 1 the receiver coil comprises a folded electrically insulative sheet of embedded conductor traces, the folded sheet wound into a spiral form.

3. The method of claim 1 wherein the receiver coil was produced by:
   etching conductor traces on an electrically insulative sheet;
   depositing an electrical insulator over the etched conductor traces sufficient to embed the etched conductor traces;
   folding the sheet over onto itself, stacking the embedded conductor traces; and then
   winding the folded sheet into the spiral.

4. The method of claim 1 further comprising:
   rectifying the second current from the receiver coil to generate a direct current.

5. The method of claim 1 wherein the second current in the receiver coil creates 25 milliwatts of power and a peak-to-peak voltage of 3.7 volts.

6. The method of claim 1 wherein the varying magnetic field is about 10 MHz.

7. The method of claim 1 further comprising:
   generating the varying magnetic field using a transmitter coil.

8. The method of claim 1 wherein the intraocular device includes:
   a processing circuit; and
   an array of stimulating electrodes adapted to be connected with inner-retina neurons in the eye.

9. The method of claim 1 wherein the receiver coil has an outer diameter equal to or less than 10 millimeters, an inner diameter equal to or greater than 6 millimeters, and a cross section thickness equal to or less than 1 millimeter.

10. The method of claim 1 wherein the receiver coil has an equivalent mass equal to or less than 10 milligrams in aqueous solution.

11. The method of claim 1 further comprising:
buoyantly supporting the receiver coil within the lens capsule using a chamber sealed with air.

12. The method of claim 2 wherein the electrically insulative sheet and embedded conductor traces are biocompatible.

13. The method of claim 2 wherein one or more longitudinal creases in the electrically insulative sheet are pre-formed between the conductor traces.

14. The method of claim 2 wherein a first conductor trace on the receiver coil at an axially outermost position on a fold travels across a longitudinal fold crease and an adjacent second conductor trace travels into the axially outermost position.

15. The method of claim 2 wherein the electrically insulative sheet is folded longitudinally along two creases.

16. The method of claim 2 wherein the conductor traces on the electrically insulative sheet included at one time a U-shaped region connecting two lengths of conductor traces that projected in a same direction from the U-shaped region, the folded sheet created by:
folding the insulative sheet, before the winding, such that the U-shaped region is perpendicular to the rest of the insulative sheet; and then
folding the U-shaped region such that the lengths of conductor traces project in opposite directions from the U-shaped region.

17. The method of claim 1 further comprising:
buoyantly supporting the receiver coil within the lens capsule using a ring-shaped sealed cavity.

18. The method of claim 1 wherein the conductor traces are embedded in parylene C.

19. The method of claim 7 wherein the transmitter coil is supported by an externally supported stand.

20. The method of claim 1 further comprising:
pinching the receiver coil in order to implant within the lens capsule.

* * * * *